US012143379B2

(12) United States Patent
Tada et al.

(10) Patent No.: US 12,143,379 B2
(45) Date of Patent: Nov. 12, 2024

(54) BIOMETRIC AUTHENTICATION SYSTEM AND LIVING BODY INFORMATION DETECTION DEVICE

(71) Applicant: Japan Display Inc., Tokyo (JP)

(72) Inventors: Masahiro Tada, Tokyo (JP); Takashi Nakamura, Tokyo (JP); Akio Takimoto, Tokyo (JP); Tomokatsu Kinugawa, Tokyo (JP)

(73) Assignee: JAPAN DISPLAY INC., Tokyo (JP)

( * ) Notice: Subject to any disclaimer, the term of this patent is extended or adjusted under 35 U.S.C. 154(b) by 447 days.

(21) Appl. No.: 17/488,295

(22) Filed: Sep. 29, 2021

(65) Prior Publication Data

US 2022/0021669 A1 Jan. 20, 2022

Related U.S. Application Data

(63) Continuation of application No. PCT/JP2020/004661, filed on Feb. 6, 2020.

(30) Foreign Application Priority Data

Apr. 2, 2019 (JP) ................. 2019-070821

(51) Int. Cl.
| | |
|---|---|
| *H04L 9/40* | (2022.01) |
| *G06F 3/041* | (2006.01) |
| *G06V 10/141* | (2022.01) |
| *G06V 40/12* | (2022.01) |
| *G06V 40/13* | (2022.01) |

(52) U.S. Cl.
CPC ...... *H04L 63/0861* (2013.01); *G06F 3/04164* (2019.05); *G06F 3/04166* (2019.05); *G06V 10/141* (2022.01); *G06V 40/1318* (2022.01); *G06V 40/1394* (2022.01)

(58) Field of Classification Search
None
See application file for complete search history.

(56) References Cited

U.S. PATENT DOCUMENTS

| | | | | |
|---|---|---|---|---|
| 7,068,254 | B2* | 6/2006 | Yamazaki | G06V 40/1318 |
| | | | | 345/104 |
| 2006/0050931 | A1* | 3/2006 | Oka | G07C 9/37 |
| | | | | 382/115 |

(Continued)

FOREIGN PATENT DOCUMENTS

| | | |
|---|---|---|
| JP | 2002-91920 A | 3/2002 |
| JP | 2003-91510 A | 3/2003 |

OTHER PUBLICATIONS

International Search Report and Written Opinion mailed on Apr. 7, 2020, received for PCT Application PCT/JP2020/004661, Filed on Feb. 6, 2020, 8 pages including English Translation.

(Continued)

*Primary Examiner* — Kaveh Abrishamkar
(74) *Attorney, Agent, or Firm* — XSENSUS LLP

(57) ABSTRACT

A biometric authentication system is a biometric authentication system having a detection device and an authentication device performing personal authentication. The detection device has a plurality of sensor elements, a plurality of gate lines and a plurality of signal lines provided in correspondence with the sensor elements, and gate line drive circuit scanning the gate lines.

11 Claims, 16 Drawing Sheets

(56) References Cited

U.S. PATENT DOCUMENTS

| | | | | |
|---|---|---|---|---|
| 2006/0182318 A1* | 8/2006 | Shigeta | .............. | G06V 40/1335 |
| | | | | 382/124 |
| 2010/0328269 A1* | 12/2010 | Kurokawa | ............ | G06F 3/0416 |
| | | | | 345/175 |
| 2011/0001725 A1* | 1/2011 | Kurokawa | .............. | G06F 3/042 |
| | | | | 345/82 |
| 2017/0286739 A1* | 10/2017 | Shibano | ............. | G06V 40/1306 |
| 2017/0300736 A1* | 10/2017 | Song | ................. | G06V 40/1312 |
| 2022/0021669 A1* | 1/2022 | Tada | .................... | G06V 10/141 |

OTHER PUBLICATIONS

Chinese Office Action issued Dec. 21, 2023 with machine translation in corresponding Chinese patent application No. 202080025949.0, 15 pages.

\* cited by examiner

BIOMETRIC AUTHENTICATION SYSTEM AND LIVING BODY INFORMATION DETECTION DEVICE

CROSS-REFERENCE TO RELATED APPLICATIONS

This application is a continuation of PCT international application Ser. No. PCT/JP2020/004661 filed on Feb. 6, 2020 which designates the United States, incorporated herein by reference, and which claims the benefit of priority from Japanese Patent Application No. 2019-070821, filed on Apr. 2, 2019, incorporated herein by reference.

BACKGROUND

1. Technical Field

The present disclosure relates to a biometric authentication system and a living body information detection device.

2. Description of the Related Art

Biometric authentication systems that detect living body information such as a fingerprint or venous pattern by a sensor to perform personal authentication have been known (refer to Japanese Patent Application Laid-open Publication No. 2002-91920, for example). In the method of personal authentication described in Japanese Patent Application Laid-open Publication No. 2002-91920, a living body information acquisition device and an authentication device perform communications via a network. The living body information acquisition device encodes acquired living body information based on a processing key and transmits the encoded living body information to the acquisition device. The authentication device receives the encoded living body information and inversely converts the encoded living body information to perform personal authentication.

The method encrypting or encoding the living body information can inhibit the possibility of the living body information leaking on the network. However, the living body information acquisition device may hold detected living body information, that is, living body information not encrypted or encoded, or living body information registered in advance. Thus, there is a possibility of the living body information leaking from the living body information acquisition device.

SUMMARY

A biometric authentication system according to an embodiment of the present disclosure includes a detection device configured to acquire living body information, and an authentication device coupled to the detection device via a network and configured to perform personal authentication. The detection device has a plurality of sensor elements, a plurality of gate lines and a plurality of signal lines provided in correspondence with the sensor elements, and a gate line drive circuit scanning the gate lines, the authentication device has a memory storing therein a sensor control code controlling the sensor elements and registered living body information as living body information registered in advance, a sensor control code setter configured to set the sensor control code when receiving, from the detection device, an authentication request signal to start authentication, and a communicator configured to transmit the sensor control code to the detection device, the sensor control code includes a plurality of selection modes of the gate lines, and the gate line drive circuit scans the gate lines based on the sensor control code received from the authentication device.

A living body information detection device according to an embodiment of the present disclosure includes a plurality of sensor elements, a plurality of gate lines and a plurality of signal lines provided in correspondence with the sensor elements, and a gate line drive circuit scanning the gate lines. The gate line drive circuit scans the gate lines based on a sensor control code that is supplied from the outside and includes a plurality of selection modes of the gate lines.

DETAILED DESCRIPTION

The following describes aspects (embodiments) to perform the disclosure in detail with reference to the accompanying drawings. The details described in the following embodiments do not limit the present disclosure. The components described in the following include components that can easily be thought of by those skilled in the art and components that are substantially the same. Furthermore, the components described in the following can be combined with each other as appropriate. The disclosure is only by way of example, and some appropriate modifications with the gist of the disclosure maintained that can easily be thought of by those skilled in the art are naturally included in the scope of the present disclosure. The drawings may be represented more schematically for the width, thickness, shape, and the like of parts than those of actual aspects in order to make the description clearer; they are only by way of example and do not limit the interpretation of the present disclosure. In the present specification and drawings, components similar to those previously described for the drawings previously described are denoted by the same symbols, and a detailed description may be omitted as appropriate.

Embodiment

Figure 1:
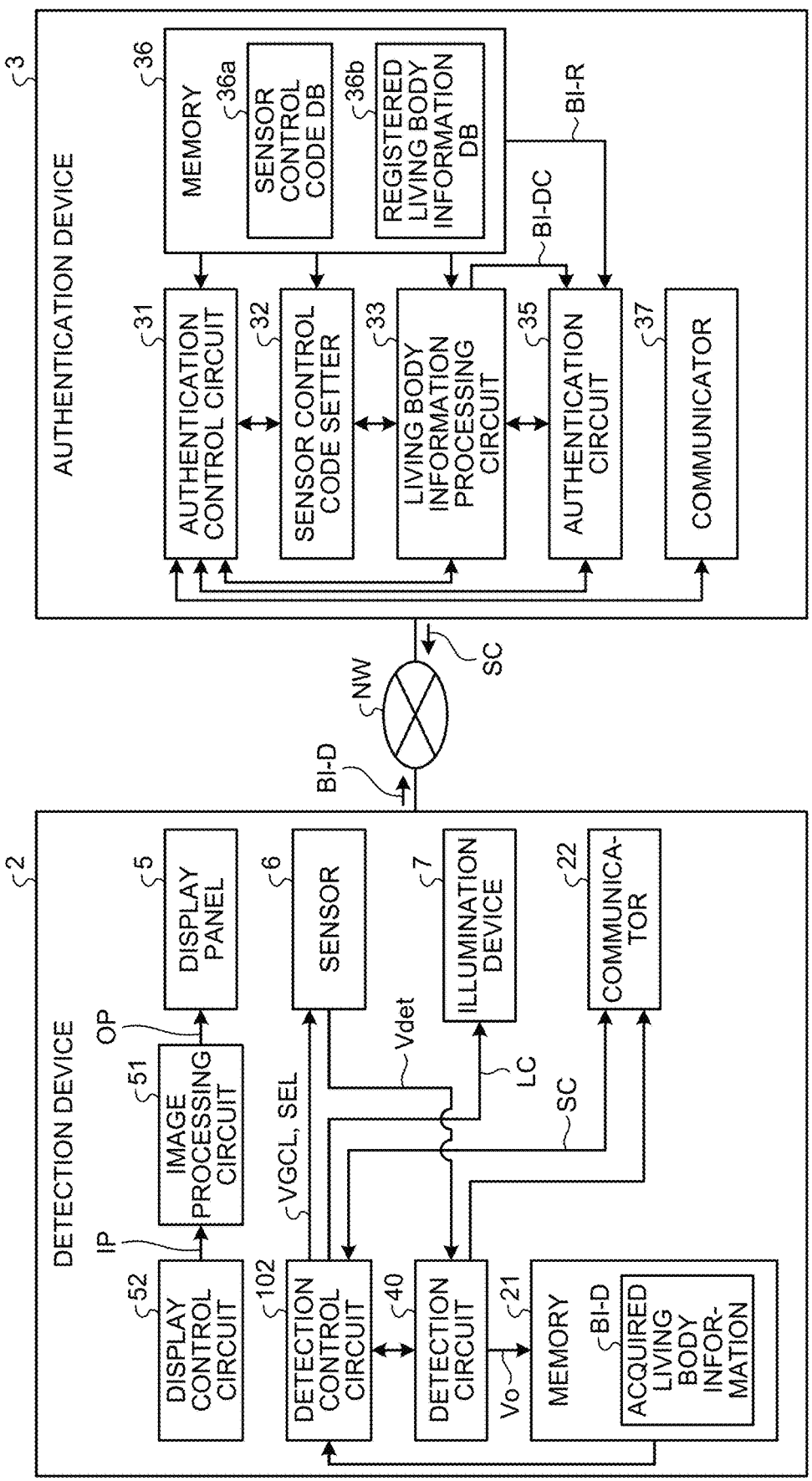
FIG. 1 is a block diagram of a configuration example of a biometric authentication system according to an embodiment.

FIG. 1 is a block diagram of a configuration example of a biometric authentication system according to an embodiment. As illustrated in FIG. 1, this biometric authentication system 1 has a detection device 2 and an authentication device 3. The detection device 2 is a device acquiring acquired living body information BI-D as living body information. The authentication device 3 is a device receiving the acquired living body information BI-D to perform personal authentication. The detection device 2 and the authentication device 3 are coupled to each other via a network NW. The network NW is a communication unit such as the Internet or a wireless unit.

The detection device 2 may be the detection device 2 as a single device having communication functionality, be one incorporated into a portable terminal such as a smartphone, a smart watch, a tablet terminal, or a cellular phone, or be one included in an electronic apparatus such as a personal computer, an automatic teller machine (ATM), an entrance management device, or an IC card.

The detection device 2 illustrated in FIG. 1 includes a display panel 5, a sensor 6, an illumination device 7, a memory 21, a communicator 22, an image processing circuit 51, a display control circuit 52, a detection control circuit 102, and a detection circuit 40. The display panel 5 displays various kinds of information such as an authentication request and an authentication result transmitted from the authentication device 3. The display panel 5 is a liquid crystal display panel including a liquid crystal layer as a display element, for example. However, the display panel 5 is not limited to this example and may be another display panel such as an organic electroluminescence (EL) display or micro-light emitting diode (LED) (μLED) display including an organic light emitting diode (OLED) as a display element or an electrophoretic display (EPD) including an electrophoretic element as a display element. The display panel 5 may have a touch sensor detecting contact or proximity of a finger Fg. The sensor 6 may have a function of the touch sensor detecting contact or proximity of the finger Fg. The detection device 2 does not necessarily have the display panel 5.

The display control circuit 52 is a circuit controlling the display of the display panel 5. The display control circuit 52 is a micro-processing unit (MPU), for example. The image processing circuit 51 performs output of various kinds of signals based on an input signal IP input from the display control circuit 52. The input signal IP includes a signal for displaying an image (an RGB image signal, for example). In displaying, the image processing circuit 51 generates an image signal OP based on the input signal IP and outputs the image signal OP to the display panel 5.

The sensor 6 is a device acquiring various kinds of living body information such as a fingerprint and a venous pattern. The sensor 6 has a plurality of sensor elements PD and acquires the acquired living body information BI-D based on signals detected for the respective sensor elements PD. The sensor elements PD are each a photoelectric conversion element outputting a signal corresponding to applied light. The sensor 6 is not limited to an optical sensor and may be another detection system such as a capacitance type sensor.

The illumination device 7 applies light L1 toward an object to be detected such as the finger Fg. The illumination device 7 may be a backlight of what is called a side light type having a light guide plate provided at a position corresponding to a detection area AA (refer to FIG. 2) and a plurality of light sources arranged on one end or both ends of the light guide plate, for example. As the light sources, light emitting diodes (LEDs) emitting light with a certain color are used, for example. The illumination device 7 may be a backlight of what is called a directly under type backlight having a light source (an LED, for example) provided directly under the detection area AA. The illumination device 7, which is not limited to the backlight, may be provided on a side or above the sensor 6 and may apply the light L1 from the side of or above the finger Fg. The display panel 5 and the sensor may be superimposed on each other to use the display panel 5 as a light source.

The detection control circuit 102 is a circuit supplying various kinds of signals to the sensor 6 and the illumination device 7 to control acquisition of the living body information. The detection control circuit 102 performs an authentication request and the like in cooperation with the display control circuit 52. The detection control circuit 102 may include the MPU forming the display control circuit 52, for example. The detection control circuit 102 outputs a gate drive signal VGCL and a selection signal SEL to the sensor 6 based on a sensor control code SC transmitted from the authentication device 3. Thus, the sensor 6 is driven by a system based on the sensor control code SC. The detection control circuit 102 outputs an illumination control signal LC to the illumination device 7 based on the sensor control code SC transmitted from the authentication device 3. Thus, the illumination device 7 emits the light L1 having a wavelength, a light amount and luminance, the frequency of on and off, and the like corresponding to the illumination control signal LC.

The detection circuit 40 is a circuit performing signal processing of a detection signal Vdet detected by the sensor 6 based on the sensor control code SC. The memory 21 is a circuit storing therein the acquired living body information BI-D. The memory 21 stores therein a sensor output signal Vo successively output from the detection circuit 40 as the acquired living body information BI-D. As the memory 21, various kinds of storage devices such as a semiconductor memory and a hard disk drive can be used, for example.

The communicator 22 has a network interface controller for performing communications corresponding to a protocol employed by the network NW. The communicator 22 is coupled to the network NW to perform processing on communications.

The authentication device 3 has an authentication control circuit 31, a sensor control code setter 32, a living body information processing circuit 33, an authentication circuit 35, a memory 36, and a communicator 37. The authentication device 3 may be a server device provided in the network NW or an electronic apparatus such as a smartphone or a personal computer.

The memory 36 stores therein a sensor control code database 36a and a registered living body information database 36b. The sensor control code database 36a includes information on the sensor control code SC. The sensor control code SC includes various kinds of information such as a plurality of selection modes for controlling driving of gate lines GCL. The registered living body information database 36b includes a plurality of pieces of registered living body information BI-R registered in advance for each user of the biometric authentication system 1. The registered living body information database 36b may include a plurality of kinds of pieces of living body information such as a fingerprint and a venous pattern on one user.

The authentication control circuit 31 is a circuit supplying a control signal to the circuits of the authentication device 3 to control authentication of the living body information. The sensor control code setter 32 sets the sensor control code SC corresponding to the living body information to be detected out of a plurality of the sensor control codes SC stored in the memory 36 based on the control signal from the authentication control circuit 31. The sensor control code setter 32 transmits the set sensor control code SC to the living body information processing circuit 33 and transmits the set sensor control code SC to the detection device 2 via the communicator 37.

The living body information processing circuit 33 receives the acquired living body information BI-D transmitted from the detection device 2. The living body information processing circuit 33 performs information processing on the acquired living body information BI-D based on the set sensor control code SC. The living body information processing circuit 33 outputs living body information BI-DC after conversion to the authentication circuit 35.

The authentication circuit 35 compares the living body information BI-DC after conversion and the registered living body information BI-R acquired from the memory 36 with each other to perform personal authentication. The authentication circuit 35 transmits an authentication result to the detection device 2 via the communicator 37.

The detection device 2 receives the authentication result from the authentication device 3 to perform a certain operation corresponding to the authentication result. When the personal authentication matches, the detection device 2 permits access to various kinds of apparatuses and the network NW, for example. When the personal authentication does not match, the detection device 2 may display a result of authentication mismatch by the display panel 5 and make another authentication request to the user. In this case, the sensor control code SC can be changed.

Figure 2:
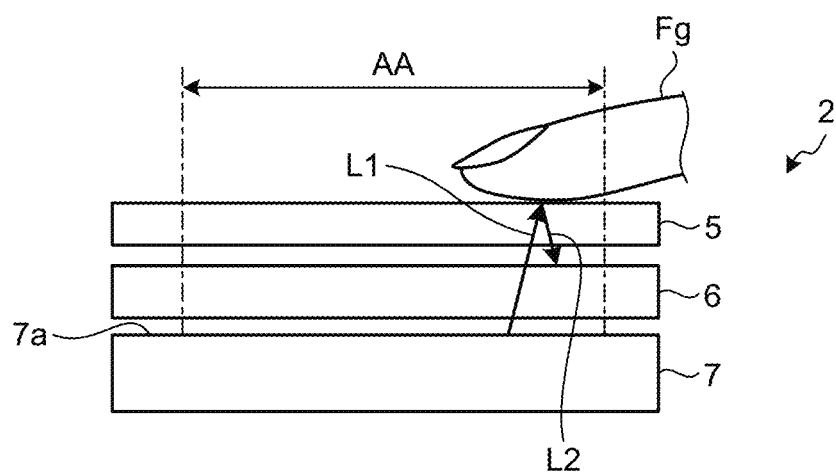
FIG. 2 is a sectional view of a schematic sectional configuration of a detection device.

The following describes configurations of the detection device 2 and the sensor 6. FIG. 2 is a sectional view of a schematic sectional configuration of the detection device. As illustrated in FIG. 2, in the detection device 2, the illumination device 7, the sensor 6, and the display panel 5 are stacked on each other in this order in a direction perpendicular to the surface of the sensor 6.

The illumination device 7 has a light application face 7a applying light and applies the light L1 from the light application face 7a toward the sensor 6. The sensor 6 is provided facing the light application face 7a of the illumination device 7. In other words, the sensor 6 is provided between the illumination device 7 and the display panel 5.

The light L1 applied from the illumination device 7 passes through the sensor 6 and the display panel 5. The sensor 6 detects light L2 reflected by the object to be detected such as the finger Fg and can thereby detect the living body information of the finger Fg or the like, for example. The living body information is, for example, a fingerprint, an image of blood vessels such as veins (a venous pattern), pulsation, a pulse wave, a blood condition (a blood oxygen concentration and the like), and the like. The color of the light L1 from the illumination device 7 may be varied in accordance with the object to be detected. The illumination device 7 can apply the light L1 of visible light (blue or green, for example) in the case of fingerprint detection, whereas the illumination device 7 can apply the light L1 of infrared light in the case of vein detection, for example.

When the display panel 5 is a liquid crystal display panel, the display panel 5 may perform displaying with the light L1 applied from the illumination device 7. That is to say, the illumination device 7 may serve both as the light source of the sensor 6 and the backlight of the display panel 5. When the display panel 5 is an organic EL panel, the detection device 2 does not necessarily include the illumination device 7, and the OLED as the display element of the display panel 5 may serve also as the illumination device 7. Although in FIG. 2 the size of the display panel 5 and the size of the sensor 6 are made the same, the sensor 6 may be superimposed on part of the display panel 5. The display panel 5 and the sensor 6 are not necessarily superimposed on each other, and the display panel 5 and the sensor 6 may be placed shifted from each other.

Figure 3:
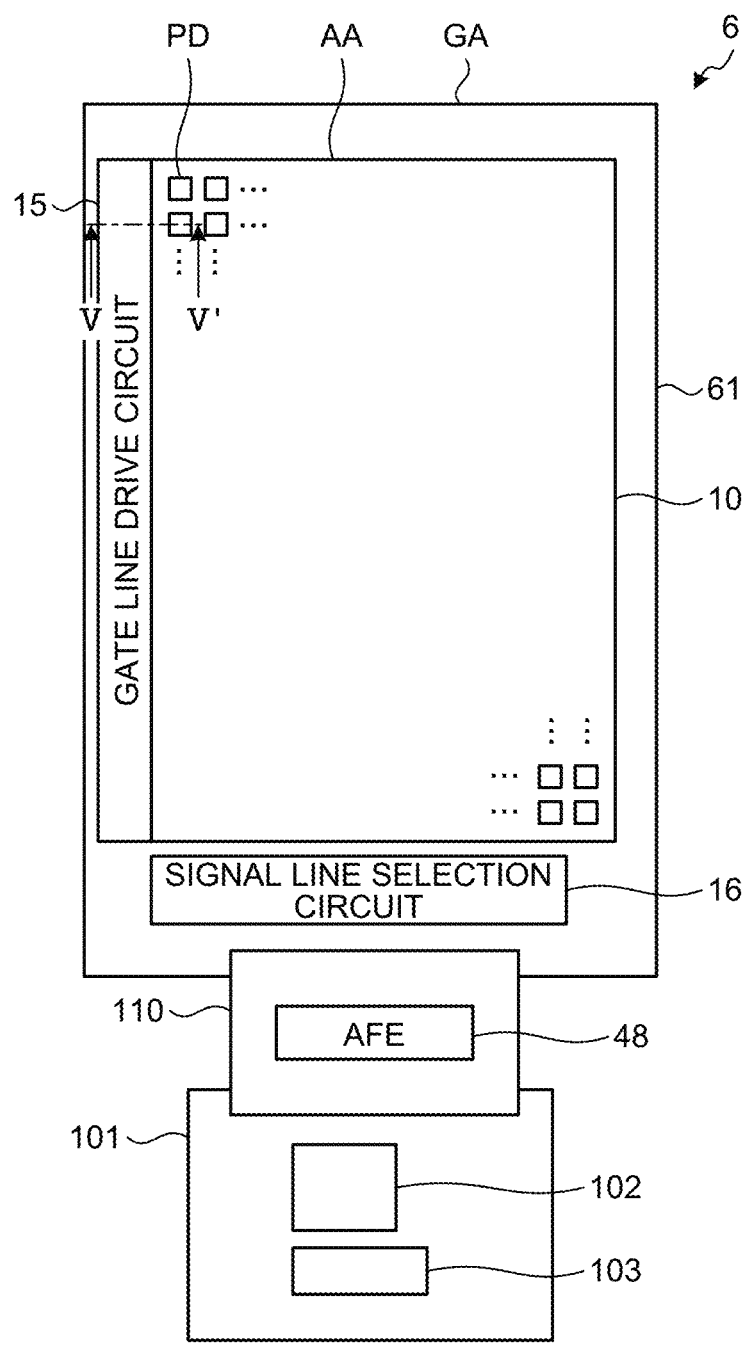
FIG. 3 is a plan view of a sensor of the detection device.
Figure 4:
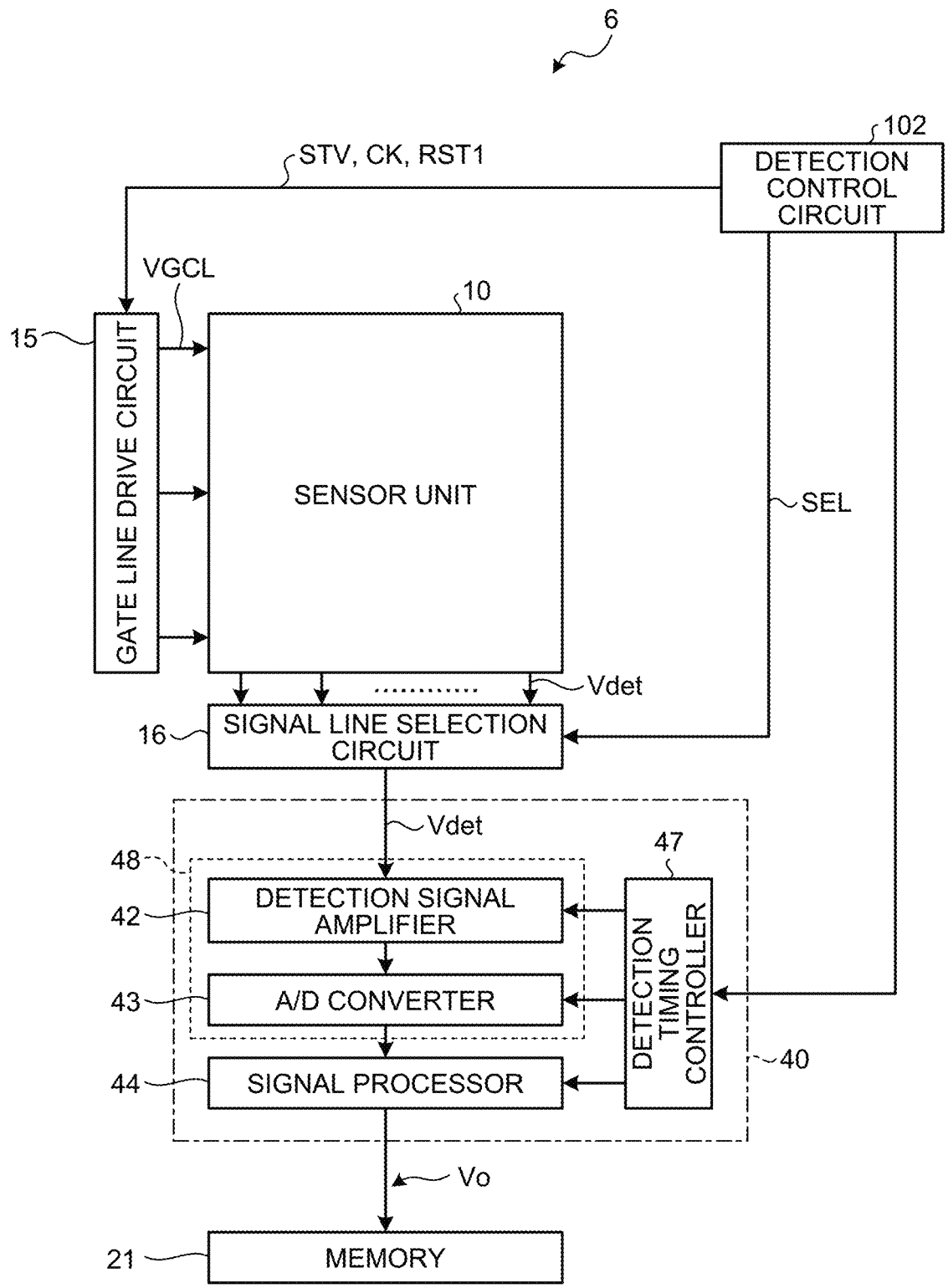
FIG. 4 is a block diagram of a configuration example of the sensor.

FIG. 3 is a plan view of the sensor of the detection device. FIG. 4 is a block diagram of a configuration example of the sensor. As illustrated in FIG. 3, the sensor 6 has a base 61, a sensor unit 10, a gate line drive circuit 15, a signal line selection circuit 16, and an analog front end circuit (hereinafter, represented as AFE) 48.

A control substrate 101 is electrically coupled to the base 61 via a flexible printed board 110. The flexible printed board 110 is provided with the AFE 48. The control substrate 101 is provided with the detection control circuit 102 and a power supply circuit 103. The detection control circuit 102 supplies a control signal to the AFE 48, the sensor unit 10, the gate line drive circuit 15, and the signal line selection circuit 16 to control a detection operation of the sensor unit 10. The power supply circuit 103 supplies a voltage signal such as a power supply signal VDDSNS (refer to FIG. 7) to the AFE 48, the sensor unit 10, and the gate line drive circuit 15.

The base 61 has the detection area AA and a peripheral area GA. The detection area AA is an area overlapping with the sensor elements PD of the sensor unit 10. The sensor unit 10 is an optical sensor having the sensor elements PD as the photoelectric conversion element. The sensor elements PD are arranged in a matrix (row-column configuration) in the detection area AA. The peripheral area GA is an area outside the detection area AA and is an area not overlapping with the sensor elements PD. That is to say, the peripheral area GA is an area between a perimeter of the detection area AA and ends of the base 61. The gate line drive circuit 15 and the signal line selection circuit 16 are provided in the peripheral area GA. As described above, the sensor elements PD may be capacitance type sensors.

As illustrated in FIG. 4, the sensor elements PD of the sensor unit 10 output an electric signal corresponding to applied light as the detection signal Vdet to the signal line selection circuit 16. The sensor unit 10 performs detection in accordance with the gate drive signal VGCL supplied from the gate line drive circuit 15.

The detection control circuit 102 is a circuit supplying each control signal to the gate line drive circuit 15, the signal line selection circuit 16, and the detection circuit 40 to control the operations of these circuits. The detection control circuit 102 supplies various kinds of control signals such as a start signal STV, a clock signal CK, and a reset signal RST1 to the gate line drive circuit 15. The detection control circuit 102 supplies various kinds of control signals such as a selection signal SEL to the signal line selection circuit 16.

The gate line drive circuit 15 is a circuit scanning a plurality of gate lines GCL (refer to FIG. 6) based on the sensor control code SC received from the authentication device 3. The gate line drive circuit 15 selects the gate lines GCL successively or simultaneously and supplies the gate drive signal VGCL to the selected gate lines GCL. Thus, the gate line drive circuit 15 selects the sensor elements PD coupled to the gate lines GCL.

The signal line selection circuit 16 is a switch circuit selecting a plurality of signal lines SGL (refer to FIG. 6) successively or simultaneously based on the sensor control code SC received from the authentication device 3. The signal line selection circuit 16 couples the selected signal lines SGL and the detection circuit 40 to each other based on the selection signal SEL supplied from the detection control circuit 102. Thus, the signal line selection circuit 16 outputs the detection signal Vdet of the sensor elements PD to the detection circuit 40. The signal line selection circuit 16 is a multiplexer, for example.

The detection circuit 40 includes the AFE 48, a signal processor 44, and a detection timing controller 47. The detection timing controller 47 performs control to cause the AFE 48 and the signal processor 44 to operate in sync with each other based on the control signal supplied from the detection control circuit 102. Part or the whole of the functions of the detection circuit 40 may be included in the detection control circuit 102.

The AFE 48 is a signal processing circuit having at least the functions of a detection signal amplifier 42 and an analog-to-digital (A/D) converter 43. The detection signal amplifier 42 amplifies the detection signal Vdet. The A/D converter 43 converts an analog signal output from the detection signal amplifier 42 into a digital signal.

The signal processor 44 is a logical circuit detecting a certain physical quantity input to the sensor unit 10 based on an output signal of the AFE 48. The signal processor 44 can detect recesses and protrusions on the surface of the finger Fg or a palm based on the signal from the AFE 48 when the finger Fg comes in contact with or is in proximity of a detection face, for example. The signal processor 44 outputs the sensor output signal Vo in order of the sensor elements PD scanned by a drive system (the selection modes of the gate lines GCL) based on the sensor control code SC. Based on the sensor control code SC, the digital signal input to the signal processor 44 can further be processed to be output as the sensor output signal Vo.

The memory 21 successively stores therein the sensor output signal Vo computed by the signal processor 44. The acquired living body information BI-D stored in the memory 21 is information based on the detection signal Vdet output from the sensor elements PD based on the sensor control code SC. More specifically, the acquired living body information BI-D is stored as information output successively in accordance with the selection modes of the gate lines GCL, for example, without computation of detection coordinates of the sensor elements PD being performed.

Figure 5:
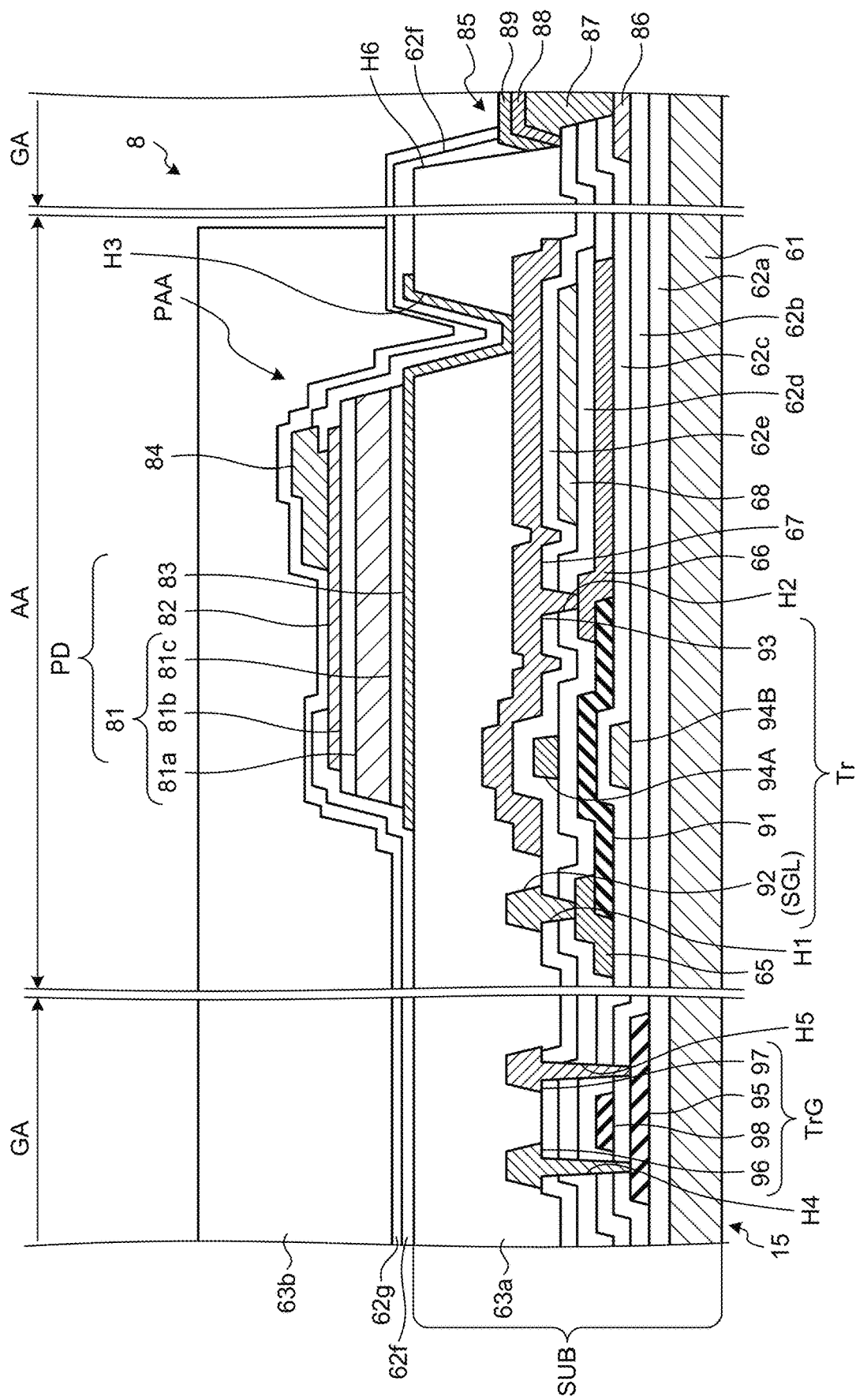
FIG. 5 is a V-V' sectional view of FIG. 3.

FIG. 5 is a V-V' sectional view of FIG. 3. FIG. 5 illustrates a section along the V-V' line and a section of a portion including a second switching element TrG of the peripheral area GA in a schematically connected manner in order to illustrate a relation between a layer structure of the detection area AA and a layer structure of the peripheral area GA. Furthermore, FIG. 5 illustrates a section of a portion including a terminal part 85 of the peripheral area GA in a schematically connected manner.

In the description of the sensor 6, in a direction perpendicular to the surface of the base 61, a direction toward the sensor elements PD from the base 61 is referred to as "upper side" or simply as "upper". A direction toward the base 61 from the sensor elements PD is referred to as "lower side" or simply as "lower". "A plan view" indicates a placement relation when viewed in the direction perpendicular to the surface of the base 61.

As illustrated in FIG. 5, a sensor element PD includes a semiconductor layer 81, an upper electrode 82, and a lower electrode 83. The sensor element PD is a positive intrinsic negative diode (PIN) type photodiode, for example.

Specifically, in the sensor element PD, the lower electrode 83, the semiconductor layer 81, and the upper electrode 82 are stacked on each other in this order on a first organic insulating layer 63a of an array substrate SUB. The array substrate SUB is a drive circuit substrate driving the sensor element PD for each certain detection area. The array substrate SUB has the base 61, a first switching element Tr provided above the base 61, the second switching element TrG, various kinds of wires, and the like.

The semiconductor layer 81 is amorphous silicon (a-Si). The semiconductor layer 81 includes an i-type semiconductor 81a, a p-type semiconductor 81b, and an n-type semiconductor 81c. The i-type semiconductor 81a, the p-type semiconductor 81b, and the n-type semiconductor 81c are specific examples of the photoelectric conversion element. In FIG. 5, the n-type semiconductor 81c, the i-type semiconductor 81a, and the p-type semiconductor 81b are stacked on each other in this order in the direction perpendicular to the surface of the base 61. However, they may have a reverse configuration; that is to say, the p-type semiconductor 81b, the i-type semiconductor 81a, and the n-type semiconductor 81c may be stacked on each other in this order.

The lower electrode 83 is a cathode of the sensor element PD and is an electrode for reading the detection signal Vdet. For the lower electrode 83, a metal material such as molybdenum (Mo) or aluminum (Al) is used, for example. Alternatively, the lower electrode 83 may be a multilayered film in which a plurality of the metal materials are stacked on each other. The lower electrode 83 may be a conductive material having translucency such as indium tin oxide (ITO).

a-Si is doped with impurities, whereby the n-type semiconductor 81c forms an n+ region. a-Si is doped with impurities, whereby the p-type semiconductor 81b forms a p+ region. The i-type semiconductor 81a is a non-doped, intrinsic semiconductor, for example, and has lower conductivity than that of the n-type semiconductor 81c and the p-type semiconductor 81b.

The upper electrode 82 is an anode of the sensor element PD and is an electrode for supplying the power supply signal VDDSNS to a photoelectric conversion layer. The upper electrode 82 is a translucent conductive layer such as ITO, and a plurality of the upper electrodes 82 are provided for the respective sensor elements PD.

As illustrated in FIG. 5, a sixth inorganic insulating layer 62f and a seventh inorganic insulating layer 62g are provided on the first organic insulating layer 63a. The sixth inorganic insulating layer 62f covers a peripheral part of the upper electrode 82 and is provided with an opening at a position overlapping with the upper electrode 82. A connection wire 84 is coupled to the upper electrode 82 at a portion of the upper electrode 82 in which the sixth inorganic insulating layer 62f is not provided. The seventh inorganic insulating layer 62g covering the upper electrode 82 and the connection wire 84 is provided on the sixth inorganic insulating layer 62f. A second organic insulting layer 63b as a flattening layer is provided on the seventh inorganic insulating layer 62g. The power supply signal VDDSNS is supplied to the upper electrode 82 via the connection wire 84.

The first switching element Tr is provided on the base 61. At least part of the first switching element Tr is provided between the base 61 and the sensor element PD. The first switching element Tr includes a first semiconductor 91, a source electrode 92, a drain electrode 93, a first gate electrode 94A, and a second gate electrode 94B. Stacked on each other on the base 61 are a first inorganic insulating layer 62a, a second inorganic insulating layer 62b, the second gate electrode 94B, a third inorganic insulating layer 62c, the first semiconductor 91, a fourth inorganic insulating layer 62d, the first gate electrode 94A, a fifth inorganic insulating layer 62e, the source electrode 92, and the drain electrode 93 in this order.

The first semiconductor 91 is an oxide semiconductor. More preferably, the first semiconductor 91 is a transparent amorphous oxide semiconductor (TAOS) out of oxide semiconductors. The oxide semiconductor is used for the first switching element Tr, whereby a leak current of the first switching element Tr can be inhibited.

The first semiconductor 91 is provided between the first gate electrode 94A and the second gate electrode 94B in a direction perpendicular to the base 61. That is to say, the first switching element Tr has what is called a dual gate structure. However, the first switching element Tr may have a top gate structure, in which the first gate electrode 94A is provided, whereas the second gate electrode 94B is not provided, or have a bottom gate structure, in which the first gate electrode 94A is not provided, whereas only the second gate electrode 94B is provided.

A first conductive layer 65 is provided covering an end of the first semiconductor 91 coupled to the source electrode 92. A second conductive layer 66 is provided covering an end of the first semiconductor 91 coupled to the drain electrode 93. The first conductive layer 65 is exposed at a bottom of a contact hole H1. The source electrode 92 is electrically coupled to the first semiconductor 91 via the contact hole H1 and the first conductive layer 65. Similarly, the second conductive layer 66 is exposed at a bottom of a contact hole H2. The drain electrode 93 is electrically coupled to the first semiconductor 91 via the contact hole H2 and the second conductive layer 66.

A third conductive layer 67 is provided on the fifth inorganic insulating layer 62e. In the present embodiment, the drain electrode 93 is the third conductive layer 67 provided above the first semiconductor 91 via the fourth inorganic insulating layer 62d and the fifth inorganic insulating layer 62e. The lower electrode 83 of the sensor element PD is coupled to the third conductive layer 67 via a contact hole H3. That is to say, the third conductive layer 67 is electrically coupled to the lower electrode 83 as the cathode of the sensor element PD and is provided between the sensor element PD and the first gate electrode 94A of the first switching element Tr. The third conductive layer 67 has a function as a protective layer protecting the first switching element Tr.

A fourth conductive layer 68 is provided between the second conductive layer 66 and the third conductive layer 67. Thus, capacitance is formed between the second conductive layer 66 and the fourth conductive layer 68, whereas capacitance is formed between the third conductive layer 67 and the fourth conductive layer 68. The capacitance formed by the second conductive layer 66, the third conductive layer 67, and the fourth conductive layer 68 is the capacitance of a capacitance element Ca illustrated in FIG. 7.

For the first conductive layer 65 to the fourth conductive layer 68, a metal material such as aluminum (Al), copper (Cu), silver (Ag), or molybdenum (Mo) or an alloy of these metals may be used. For the inorganic insulating layers, a silicon oxide film (SiO), a silicon nitride film (SiN), a silicon oxide nitride film (SiON), or the like is used. Each of the inorganic insulating layers is not limited to a single layer and may be a multilayered film.

The peripheral area GA is provided with the second switching element TrG of the gate line drive circuit 15. The second switching element TrG is provided above the base 61 the same as the first switching element Tr. The second switching element TrG includes a second semiconductor 95, a source electrode 96, a drain electrode 97, and a gate electrode 98.

The second semiconductor 95 is polycrystalline silicon. More preferably, the second semiconductor 95 is low temperature polycrystalline silicon (hereinafter, represented as LTPS). The second semiconductor 95 is provided on the first inorganic insulating layer 62a. That is to say, the first semiconductor 91 of the first switching element Tr is provided at a position away from the base 61 than the second semiconductor 95 of the second switching element TrG is in the direction perpendicular to the base 61. However, the second semiconductor 95 may be formed of the same material as that of the first semiconductor 91 and be provided in the same layer as that of the first semiconductor 91.

The source electrode 96 is electrically coupled to the second semiconductor 95 via a contact hole H4. The drain electrode 97 is electrically coupled to the second semiconductor 95 via a contact hole H5. The semiconductors of third switching elements TrS and fourth switching elements TrR illustrated in FIG. 6 may be oxide semiconductors including TAOS.

The terminal part 85 is provided at a position different from the area of the peripheral area GA in which the gate line drive circuit 15 is provided. The terminal part 85 has a first terminal conductive layer 86, a second terminal conductive layer 87, a third terminal conductive layer 88, and a fourth terminal conductive layer 89. The first terminal conductive layer 86 is provided on the second inorganic insulating layer 62b in the same layer as that of the second gate electrode 94B. A contact hole H6 is provided by causing the third inorganic insulating layer 62c, the fourth inorganic insulating layer 62d, the fifth inorganic insulating layer 62e, and the first organic insulating layer 63a to communicate with each other.

The second terminal conductive layer 87, the third terminal conductive layer 88, and the fourth terminal conductive layer 89 are stacked on each other in this order within the contact hole H6 and are electrically coupled to the first terminal conductive layer 86. Although FIG. 5 illustrates one terminal part 85, a plurality of the terminal parts 85 are arranged with spacing. The terminal parts 85 are electrically coupled to the flexible printed board 110 (refer to FIG. 3) with an anisotropic conductive film (ACF) or the like, for example.

The sensor element PD is not limited to amorphous silicon (a-Si). The sensor element PD may be a PIN type photodiode formed of polysilicon or more preferably LTPS or be formed of an organic material, for example.

Figure 6:
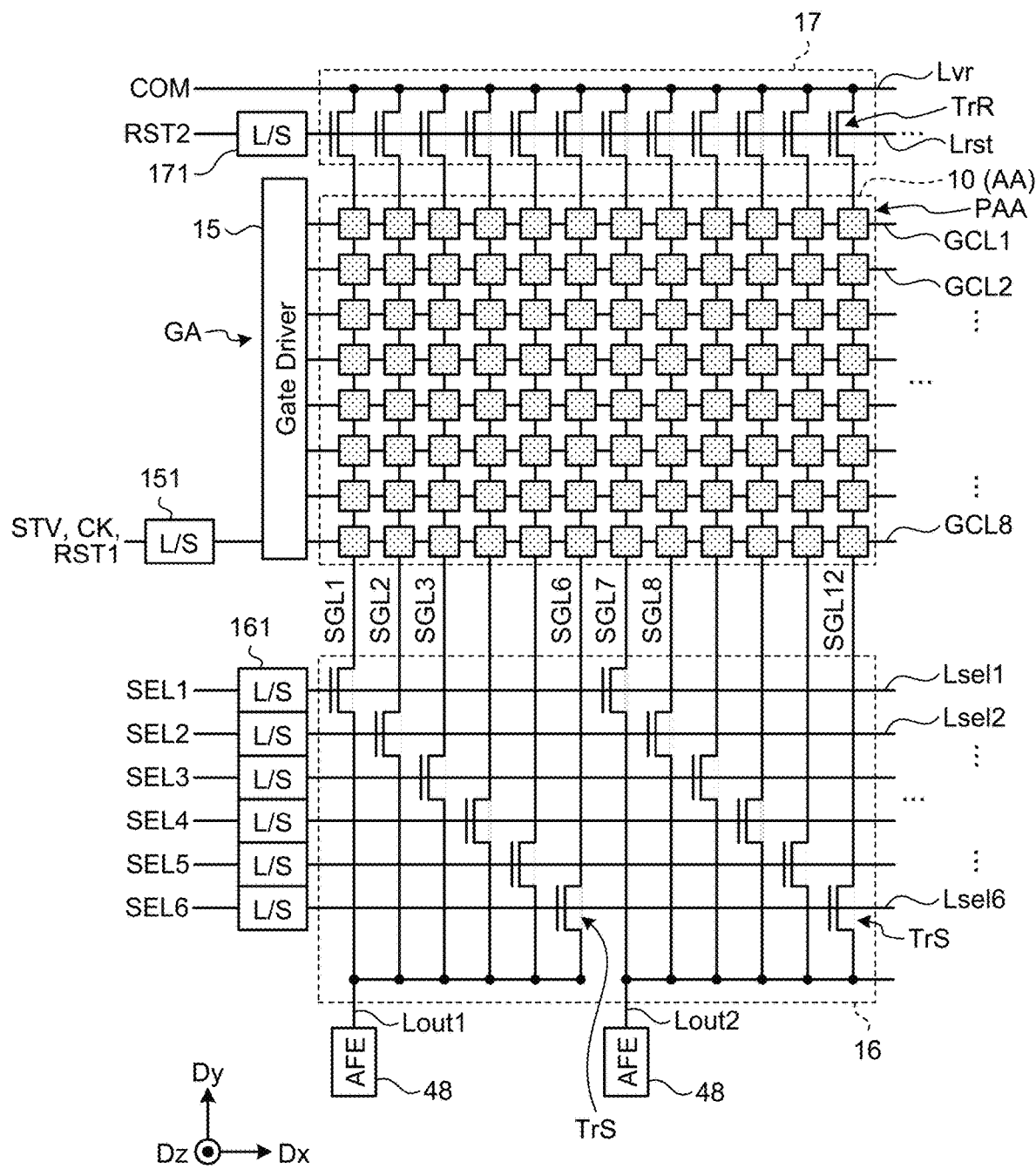
FIG. 6 is a circuit diagram of the sensor.
Figure 7:
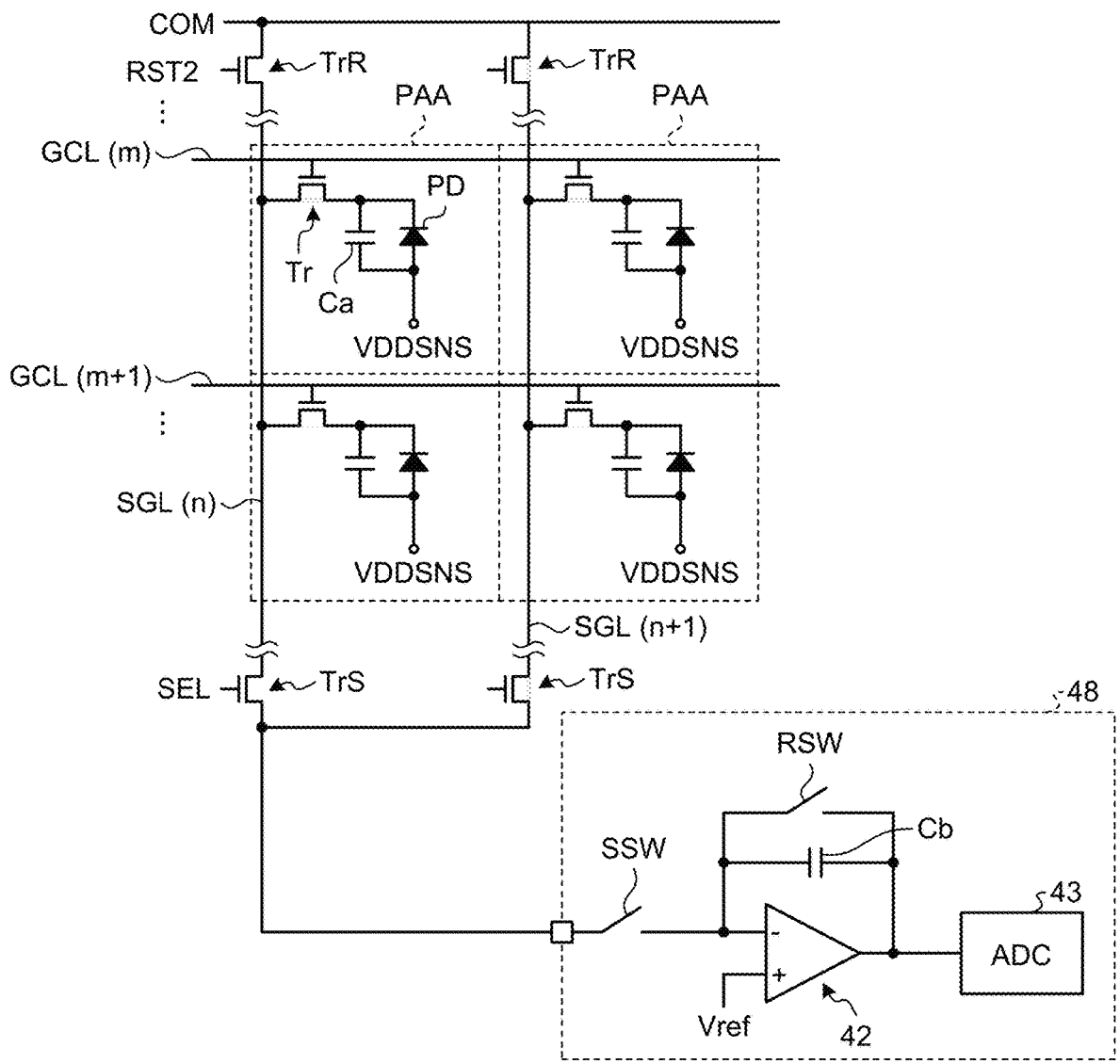
FIG. 7 is a circuit diagram of a plurality of partial detection areas.
Figure 8:
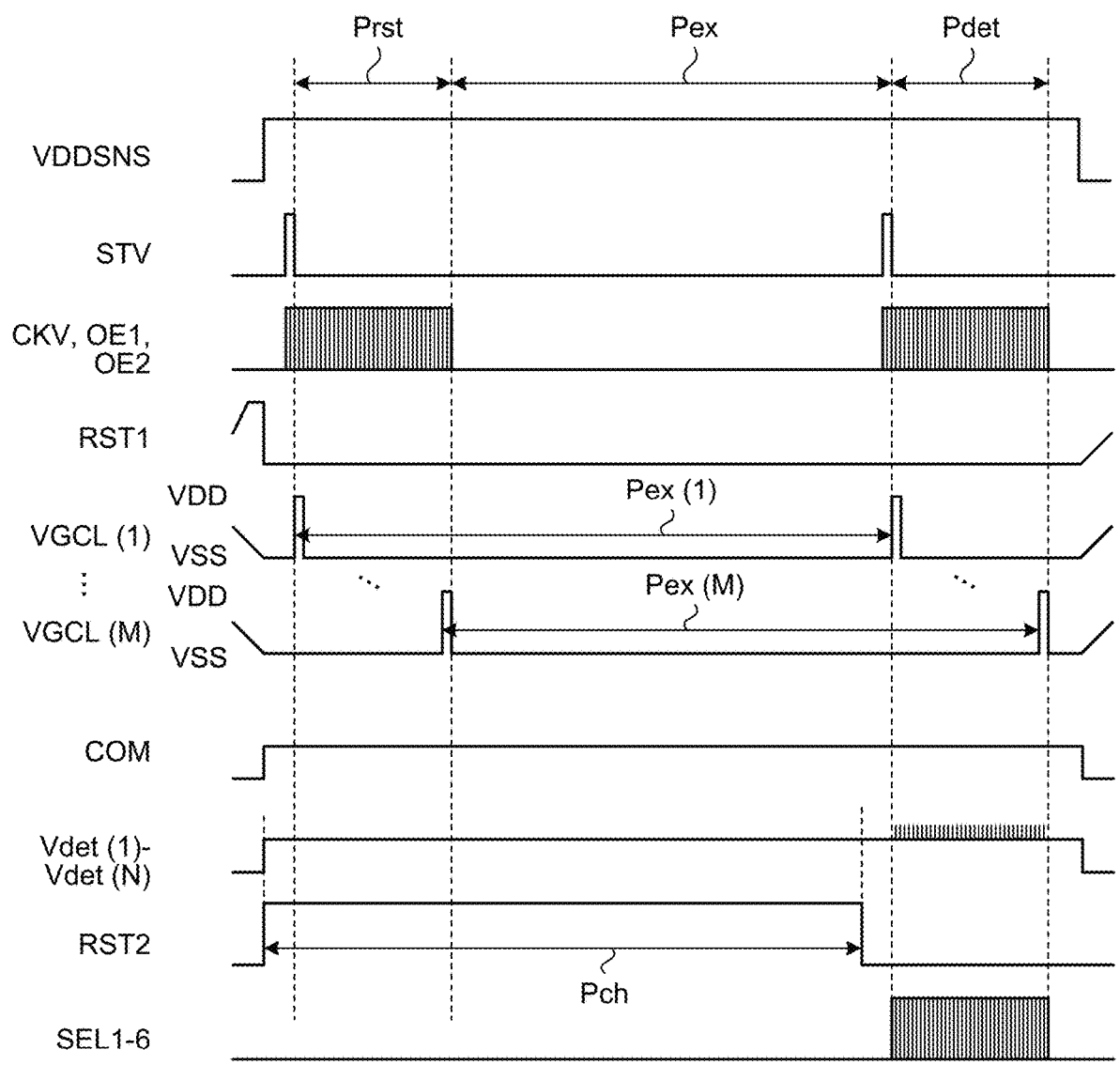
FIG. 8 is a timing waveform diagram representing an operation example of the sensor.
Figure 9:
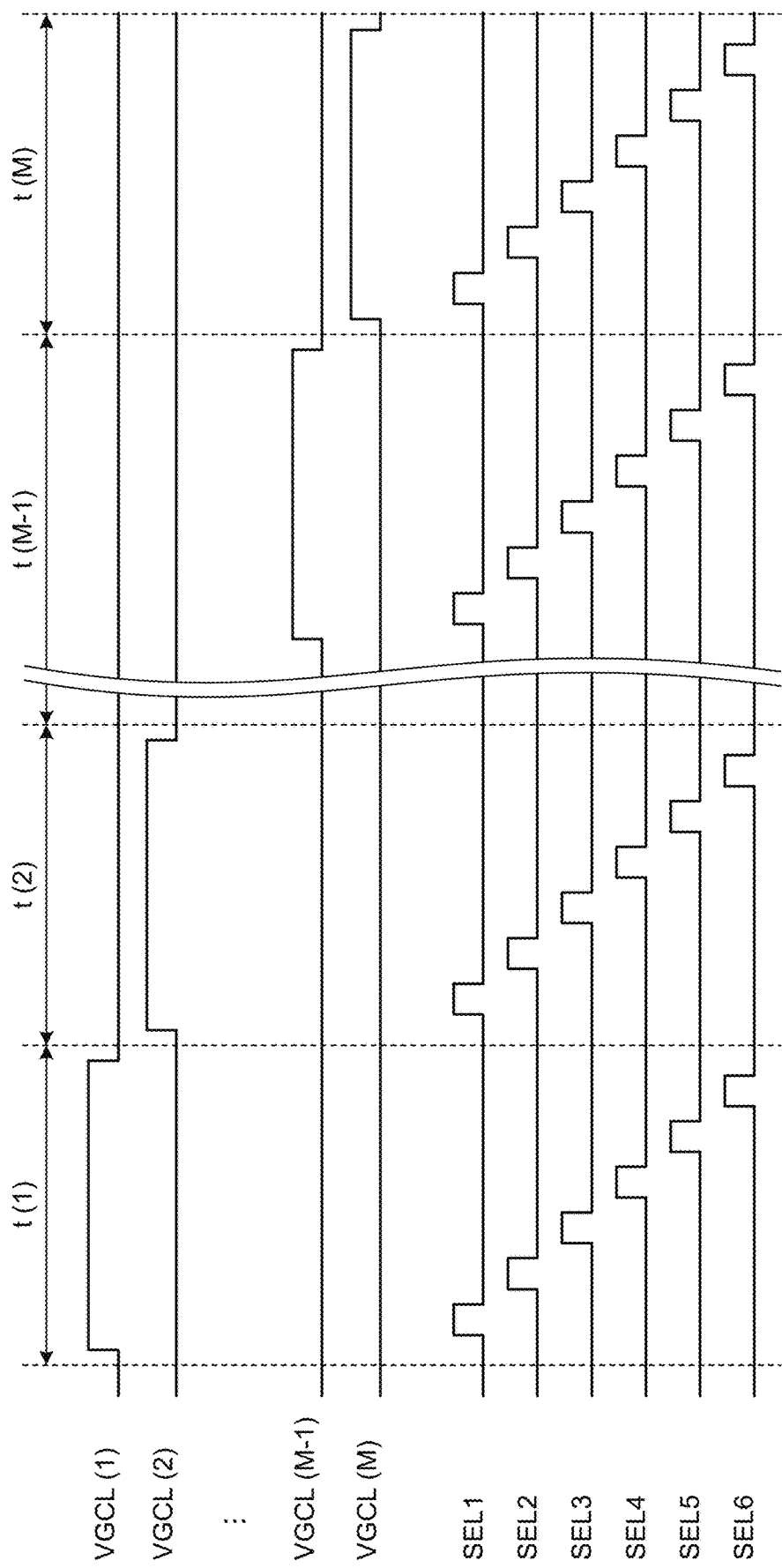
FIG. 9 is a timing waveform diagram representing an operation example of a reading period in FIG. 8.
Figure 10:
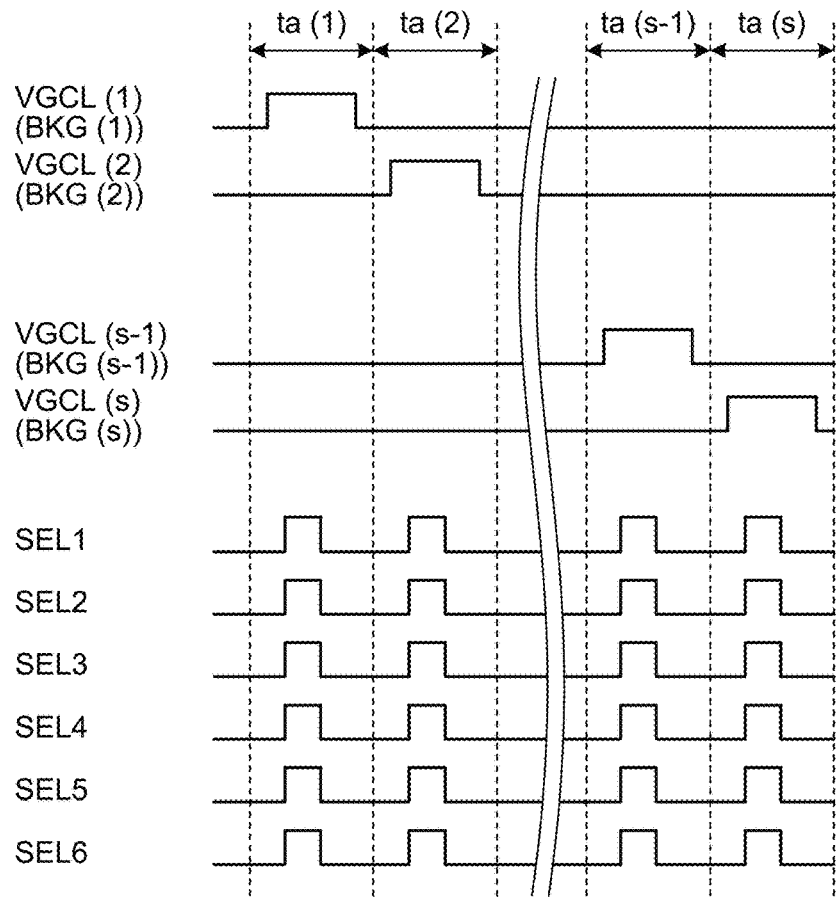
FIG. 10 is a timing waveform diagram representing an operation example of bound driving of the sensor.

The following describes a circuit configuration example and an operation example of the sensor 6. FIG. 6 is a circuit diagram of the sensor. FIG. 7 is a circuit diagram of a plurality of partial detection areas. FIG. 8 is a timing waveform diagram representing an operation example of the sensor. FIG. 9 is a timing waveform diagram representing an operation example of a reading period in FIG. 8. FIG. 10 is a timing waveform diagram representing an operation example of bound driving of the sensor.

As illustrated in FIG. 6, the sensor unit 10 has a plurality of partial detection areas PAA arranged in a matrix (row-column configuration). The partial detection areas PAA are provided with the respective sensor elements PD. The gate lines GCL and the signal lines SGL are provided in correspondence with the sensor elements PD.

The gate lines GCL extend in a first direction Dx and are coupled to the partial detection areas PAA arranged in the first direction Dx. A plurality of gate lines GCL1, GCL2, . . . , GCL8 are arranged in a second direction Dy and are each coupled to the gate line drive circuit 15. In the following description, when there is no need to describe the gate lines GCL1, GCL2, . . . , GCL8 in a discriminated manner, they are represented simply as the gate lines GCL. Although the number of the gate lines GCL is eight, it is only by way of example; M (M is eight or more; M=256, for example) gate lines GCL may be arranged.

The first direction Dx is one in-plane direction parallel to the base 61 and is a direction parallel to the gate lines GCL, for example. The second direction Dy is one in-plane direction parallel to the base 61 and is a direction orthogonal to the first direction Dx. The second direction Dy may cross the first direction Dx without being orthogonal thereto. A third direction Dz is a direction orthogonal to the first direction Dx and the second direction Dy and is the direction perpendicular to the base 61.

The signal lines SGL extend in the second direction Dy and are coupled to the partial detection areas PAA arranged in the second direction Dy. A plurality of signal lines SGL1, SGL2, . . . , SGL12 are arranged in the first direction Dx and are each coupled to the signal line selection circuit 16 and a reset circuit 17. Although the number of the signal lines SGL is 12, it is only by way of example; N (N is 12 or more; N=252, for example) signal lines SGL may be arranged. In FIG. 6, the sensor unit 10 is provided between the signal line selection circuit 16 and the reset circuit 17; this is not limiting, and the signal line selection circuit 16 and the reset circuit 17 may each be coupled to an end of the signal lines SGL in the same direction.

The gate line drive circuit 15 receives the various kinds of control signals such as the start signal STV, the clock signal CK, and the reset signal RST1 via a level shifter 151. The gate line drive circuit 15 has a plurality of the second switching elements TrG (not illustrated). The gate line drive circuit 15 selects the gate lines GCL1, GCL2, . . . , GCL8 successively in a time division manner by the operation of the second switching elements TrG. The gate line drive circuit 15 supplies the gate drive signal VGCL to a plurality of the first switching elements Tr via the selected gate lines GCL. Thus, the partial detection areas PAA arranged in the first direction Dx are selected as objects to be detected. The detection control circuit 102 generates the various control signals such as the start signal STV, the clock signal CK, and the reset signal RST1 based on the sensor control code SC.

The signal line selection circuit 16 has a plurality of selection signal lines Lsel, a plurality of output signal lines Lout, and the third switching elements TrS. The third switching elements TrS are provided in correspondence with the respective signal lines SGL. Six signal lines SGL1, SGL2, . . . , SGL6 are coupled to a common output signal line Lout1. Six signal lines SGL7, SGL8, . . . , SGL12 are coupled to a common output signal line Lout2. The output signal lines Lout1 and Lout2 are each coupled to the AFE 48.

Now, the signal lines SGL1, SGL2, . . . , SGL6 are defined as a first signal line block, whereas the signal lines SGL7, SGL8, . . . , SGL12 are defined as a second signal line block. The selection signal lines Lsel are coupled to respective gates of the third switching elements TrS included in one signal line block. One selection signal line Lsel is coupled to the gates of the third switching elements TrS of a plurality of signal line blocks.

Specifically, selection signal lines Lsel1, Lsel2, . . . , Lsel6 are coupled to the respective third switching elements TrS corresponding to the signal lines SGL1, SGL2, . . . , SGL6. The selection signal line Lsel1 is coupled to the third switching element TrS corresponding to the signal line SGL1 and the third switching element TrS corresponding to the signal line SGL7. The selection signal line Lsel2 is coupled to the third switching element TrS corresponding to the signal line SGL2 and the third switching element TrS corresponding to the signal line SGL8.

The detection control circuit 102 (refer to FIG. 4) successively supplies the selection signal SEL to the selection signal lines Lsel via level shifters 161. Thus, the signal line selection circuit 16 selects the signal lines SGL in one signal line block successively in a time division manner by the operation of the third switching elements TrS. The signal line selection circuit 16 selects the signal lines SGL one by one simultaneously in the signal line blocks. With this configuration, the sensor 6 can reduce the number of integrated circuits (ICs) including the AFE 48 or the number of terminals of the ICs. The detection control circuit 102 may successively select the signal line blocks (select SEL1, SEL2, . . . , SEL6 in this order), select the signal line blocks in reverse order (SEL6, SEL5, . . . , SEL1), or change the order to any selection order other than the above as appropriate (SEL2, SEL6, . . . , SEL1 or the like) in accordance with the sensor control code SC. Any selection order may be changed for each reading period Pdet described below or be changed at any time within the reading period Pdet.

As illustrated in FIG. 6, the reset circuit 17 has a reference signal line Lvr, a reset signal line Lrst, and the fourth switching elements TrR. The fourth switching elements TrR are provided in correspondence with the respective signal lines SGL. The reference signal line Lvr is coupled to one of sources or drains of the fourth switching elements TrR. The reset signal line Lrst is coupled to gates of the fourth switching elements TrR.

The detection control circuit 102 supplies a reset signal RST2 to the reset signal line Lrst via a level shifter 171. Thus, the fourth switching elements TrR turn on, and the signal lines SGL are electrically coupled to the reference signal line Lvr. The power supply circuit 103 supplies a reference signal COM to the reference signal line Lvr. Thus, the reference signal COM is supplied to capacitance elements Ca included in the respective partial detection areas PAA.

The gate line drive circuit 15 and the signal line selection circuit 16 may execute different selection modes for respective detection modes of fingerprint detection and a plurality of different pieces of living body information (the pulse wave, the pulsation, the image of bold vessels, the blood oxygen concentration, and the like). The gate line drive circuit 15 may drive the gate lines GCL in a bundle, for example. The signal line selection circuit 16 may couple the signal lines SGL in a bundle to the AFE 48. Thus, signals detected in detection area groups PAG1 and PAG2 are output to the AFE 48. In this case, signals from the partial detection areas PAA (the sensor elements PD) included in the detection area groups PAG1 and PAG2 are integrated to be output to the AFE 48.

As illustrated in FIG. 7, a partial detection area PAA includes the sensor element PD, the capacitance element Ca, and the first switching element Tr. FIG. 7 illustrates two gate lanes GCL(m) and GCL(m+1) arranged in the second direction Dy out of the gate lines GCL and illustrates two signal lines SGL(n) and SGL(n+1) arranged in the first direction Dx out of the signal lines SGL. The partial detection area PAA is an area surrounded by the gate lines GCL and the signal lines SGL. The first switching element Tr is provided in correspondence with the sensor element PD. The first switching element Tr includes a thin film transistor and includes an n-channel metal oxide semiconductor (MOS) type thin film transistor (TFT) in this example.

Gates of the first switching elements Tr belonging to the partial detection areas PAA arranged in the first direction Dx are coupled to the gate lines GCL. Sources of the first switching elements Tr belonging to the partial detection areas PAA arranged in the second direction Dy are coupled to the signal lines SGL. Drains of the first switching elements Tr are coupled to the sensor elements PD and the capacitance elements Ca.

The sensor power supply signal VDDSNS is supplied to the sensor elements PD from a power supply circuit 123. To the signal lines SGL and the capacitance elements Ca, the reference signal COM as an initial potential of the signal lines SGL and the capacitance elements Ca is supplied from the power supply circuit 123.

Upon application of light to the partial detection areas PAA, a current corresponding to a light amount passes through the sensor elements PD, and thereby charges are accumulated in the capacitance elements Ca. When the first switching elements Tr turn on, a current passes through the signal lines SGL in accordance with the charges accumulated in the capacitance elements Ca. The signal lines SGL are coupled to the AFE 48 via the third switching elements TrS of the signal line selection circuit 16. Thus, the sensor 6 can detect a signal corresponding to the light amount of the light applied to the sensor elements PD for each of the partial detection areas PAA or for each of the detection area groups PAG1 and PAG2.

The AFE 48, in which a switch SSW turns on in the reading period Pdet (refer to FIG. 8), is coupled to the signal lines SGL. The detection signal amplifier 42 of the AFE 48 converts current fluctuations supplied from the signal lines SGL into voltage fluctuations and amplifies them. A reference voltage Vref having a fixed potential is input to a non-inverting inputter (+) of the detection signal amplifier 42, whereas the signal lines SGL are coupled to an inverting input terminal (−). In the present embodiment, the same signal as the reference signal COM is input as the reference voltage Vref. The detection signal amplifier 42 has a capacitance element Cb and a reset switch RSW. In a reset period Prst (refer to FIG. 8), the reset switch RSW turns on, and thus the charges of the capacitance element Cb are reset.

As illustrated in FIG. 8, the sensor 6 has the reset period Prst, an exposure period Pex, and the reading period Pdet. The power supply circuit 123 supplies the sensor power supply signal VDDSNS to the sensor elements PD over the reset period Prst, the exposure period Pex, and the reading period Pdet. At a time before the reset period Prst starts, a control circuit 122 supplies the reference signal COM and the reset signal RST2 as a high-level voltage signal to the reset circuit 17. The detection control circuit 102 supplies the start signal STV to the gate line drive circuit 15, and thus the reset period Prst starts.

In the reset period Prst, the gate line drive circuit 15 successively selects the gate lines GCL based on the start signal STV, the clock signal CK, and the reset signal RST1. The gate line drive circuit 15 successively supplies the gate drive signal VGCL to the gate lines GCL. The gate drive signal VGCL has a pulse-like waveform having a power supply voltage VDD as a high-level voltage and a power supply voltage VSS as a low-level voltage. In FIG. 8, M (M=256, for example) gate lines GCL are provided, in which gate drive signals VGCL(1), . . . , VGCL(M) are successively supplied to the respective gate lines GCL.

Thus, in the reset period Prst, the capacitance elements Ca of all the partial detection areas PAA are successively electrically coupled to the signal lines SGL to be supplied with the reference signal COM. Consequently, the capacitance of the capacitance elements Ca is reset.

After the gate drive signal VGCL(M) has been supplied to the gate line GCL, the exposure period Pex starts. Actual exposure periods Pex(1), . . . , Pex(M) in the partial detection areas PAA corresponding to the respective gate lines GCL have different starting times and ending times. The exposure periods Pex(1), . . . , Pex(M) are each started at a time when the gate drive signal VGCL changes from the power supply voltage VDD with the high-level voltage to the power supply voltage VSS with the low-level voltage in the reset period Prst. The exposure periods Pex(1), . . . , Pex(M) each end at a time when the gate drive signal VGCL changes from the power supply voltage VSS to the power supply voltage VDD in the reading period Pdet. The lengths of the exposure times of the exposure periods Pex(1), . . . , Pex(M) are equal.

In the exposure period Pex, a current passes in the partial detection areas PAA in accordance with the light applied to the sensor elements PD. Consequently, charges are accumulated in the capacitance elements Ca.

At a time before the reading period Pdet starts, the detection control circuit 102 makes the reset signal RST2 have a low-level voltage. Thus, the operation of the reset circuit 17 stops. In the reading period Pdet, like the reset period Prst, the gate line drive circuit 15 successively supplies the gate drive signals VGCL(1), . . . , VGCL(M) to the gate lines GCL.

Specifically, as illustrated in FIG. 9, the gate line drive circuit 15 supplies the gate drive signal VGCL(1) with the high-level voltage (the power supply voltage VDD) to the gate line GCL(1) in a period t(1). The detection control circuit 102 successively supplies selection signals SEL1, . . . , SEL6 to the signal line selection circuit 16 in a period in which the gate drive signal VGCL(1) is the high-level voltage (the power supply voltage VDD). Thus, the signal lines SGL of the partial detection areas PAA selected by the gate drive signal VGCL(1) are coupled to the detection circuit 40 (the AEF 48) successively or simultaneously. Consequently, the detection signal Vdet is supplied to the detection circuit 40 (the AEF 48) for each of the partial detection areas PAA.

Similarly, the gate line drive circuit 15 respectively supplies the gate drive signals VGCL(2), . . . , VGCL(M−1), and VGCL(M) with the high-level voltage to the gate lines GCL(2), . . . , GCL(M−1), and GCL(M) in periods t(2), . . . , t(M−1), and t(M). That is to say, the gate line drive circuit 15 supplies the gate drive signal VGCL to the gate lines GCL for each of the periods t(1), t(2), . . . , t(M−1), and t(M). For each period in which each of the gate drive signals VGCL is the high-level voltage, the signal line selection circuit 16 successively selects the signal lines SGL based on the selection signal SEL. The signal line selection circuit 16 successively couples each of the signal lines SGL to one AFE 48. Thus, the sensor 6 can output the detection signal Vdet of all the partial detection areas PAA to the AFE 48 in the reading period Pdet.

Although FIG. 9 illustrates an example in which the gate line drive circuit 15 selects one gate line GCL for each period t, this is not limiting. The gate line drive circuit 15 may simultaneously select a certain number of, two or more gate lines GCL and successively supply the gate drive signal VGCL for each of the certain number of gate lines GCL. The signal line selection circuit 16 may also simultaneously couple a certain number of, two or more signal lines SGL to one AFE 48. Furthermore, the gate line drive circuit 15 may perform scanning with a plurality of gate lines GCL omitted (with a plurality of gate lines GCL skipped).

FIG. 10 illustrates an operation example of bound driving by the gate line drive circuit 15, and the signal line selection circuit 16. As illustrated in FIG. 10, the gate line drive circuit 15 supplies the gate drive signal VGCL with the high-level voltage (the power supply voltage VDD) to a gate line block BKG(1) including the gate lines GCL in a period ta(1). The gate line block BKG(1) includes the six gate lines GCL consisting of the gate line GCL(1) to the gate line GCL(6) illustrated in FIG. 6, for example. The detection control circuit 102 simultaneously supplies the selection signals SEL1, . . . , SEL6 to the signal line selection circuit 16 in a period in which the gate drive signal VGCL is the high-level voltage (the power supply voltage VDD). Thus, the signal line selection circuit 16 simultaneously couples the six signal lines SGL to the AFE 48. Consequently, the detection signal Vdet of the detection area groups PAG1 and PAG2 illustrated in FIG. 6 is supplied to the AFE 48.

Similarly, the gate line drive circuit 15 respectively supplies gate drive signals VGCL(2), . . . , VGCL(s−1), and VGCL(s) with the high-level voltage to gate line blocks BKG(2), . . . , BKG(s−1), and BKG(s) in periods ta(2), . . . , ta(s−1), and ta(s). That is to say, the gate line drive circuit 15 simultaneously supplies the gate drive signal VGCL to the gate lines GCL for each period ta.

Thus, the sensor 6 can output the detection signal Vdet to the AFE 48 for each detection area group PAG in the reading period Pdet. The sensor 6 can increase an S/N ratio in detection compared with a case in which detection is performed for each of the partial detection areas PAA. Consequently, the sensor 6 can suitably detect information on a living body such as the image of blood vessels. In the operation example illustrated in FIG. 10, the time required for the detection of the entire area of the detection area AA can be reduced to enable quick detection, and thus a temporal change in the image of blood vessels such as the pulse wave can suitably be detected.

Although FIG. 10 illustrates an example in which the gate line drive circuit 15 drives the six gate lines GCL in a bundle, this is not limiting. The gate line drive circuit 15 may drive five or less gate lines GCL in a bundle or drive seven or more gate lines GCL in a bundle. The signal line selection circuit 16 may simultaneously couple five or less signal lines SGL to the AFE 48 or simultaneously couple seven or more signal lines SGL to the AFE 48.

The detection area groups PAG1 and PAG2 illustrated in FIG. 6 each include 6×6, or a total of 36, partial detection areas PAA (the sensor elements PD). However, the number of the partial detection areas PAA (the sensor elements PD) included in the detection area groups PAG1 and PAG2 may be 35 or less or 37 or more. In FIG. 10, the number of the gate lines GCL selected by the gate line drive circuit 15 and the number of the signal lines SGL selected by the signal line selection circuit 16 may be different from each other. That is to say, in each of the detection area groups PAG1 and PAG2, the number of the partial detection areas PAA (the sensor elements PD) arranged in the first direction Dx and the number of the partial detection areas PAA (the sensor elements PD) arranged in the second direction Dy may be different from each other.

Figure 11:
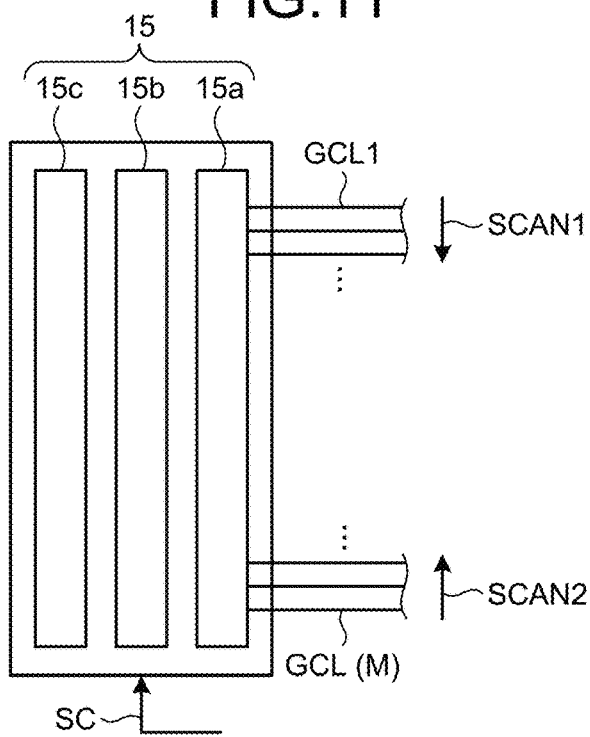
FIG. 11 is a block diagram of a configuration example of a gate line drive circuit.

FIG. 11 is a block diagram of a configuration example of the gate line drive circuit. As illustrated in FIG. 11, the gate line drive circuit 15 includes a serial access circuit 15a, a random access circuit 15b, and a CDM access circuit 15c. The gate line drive circuit 15 operates any one of the serial access circuit 15a, the random access circuit 15b, and the CDM access circuit 15c based on the selection modes of the sensor control code SC supplied from the authentication device 3. Thus, the gate line drive circuit 15 can switch a method of scanning the gate lines GCL.

As described above, the serial access circuit 15a operates so as to successively select the gate lines GCL. The serial access circuit 15a may select the gate lines GCL in a time division manner for each one gate line GCL or select the gate lines GCL in a time division manner for each gate line block BKG. The random access circuit 15b randomly selects the gate lines GCL. The random access referred to here includes various kinds of methods of access including setting access order of all the gate lines GCL to be selected and setting any starting position and successively selecting certain gate lines GCL from the starting position. The CDM access circuit 15c selects certain gate lines GCL out of the gate lines GCL based on a certain code. The sensor 6 may detect the living body information by code division multiplexing drive (hereinafter, represented as CDM drive) by the CDM access circuit 15c.

Figure 12:
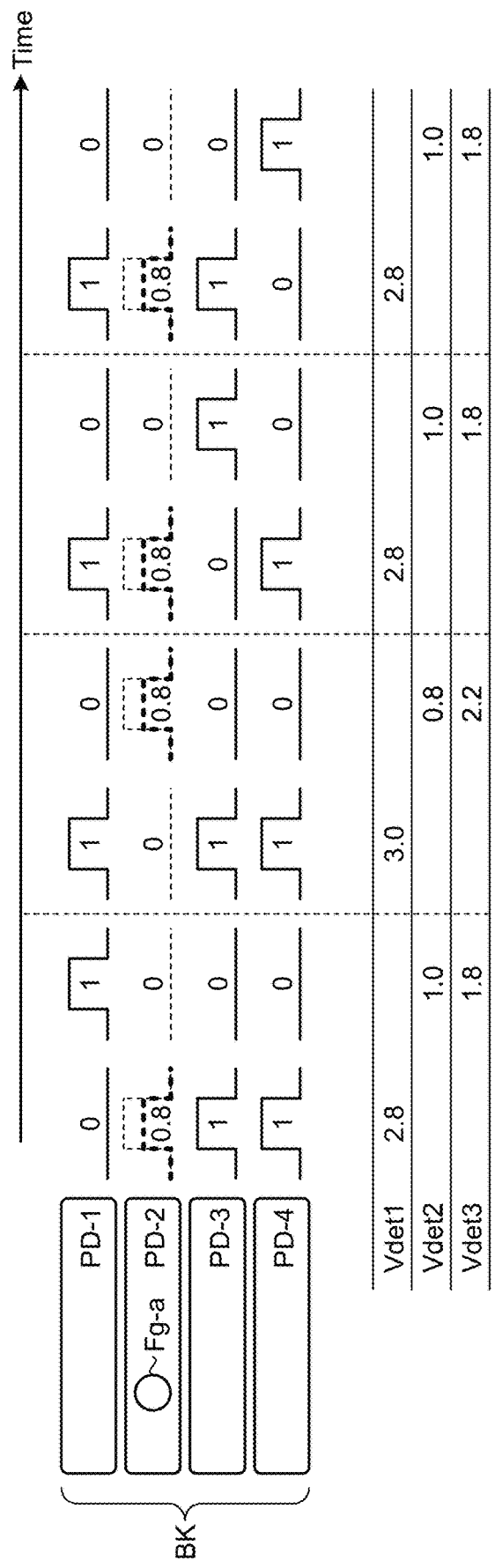
FIG. 12 is an illustrative diagram for illustrating an operation example of CDM drive.

FIG. 12 is an illustrative diagram for illustrating an operation example of the CDM drive. FIG. 12 illustrates the operation example of the CDM drive for four sensor elements PD-1, PD-2, PD-3, and PD-4 in order to make the description easy to understand. As illustrated in FIG. 12, the CDM access circuit 15c (refer to FIG. 11) selects a sensor element PD determined based on the certain code out of the four sensor elements PD-1, PD-2, PD-3, and PD-4 of a sensor element block BK. The gate drive signal VGCL is supplied to the gate line GCL corresponding to the selected sensor element PD.

The certain code is defined by a square matrix of Expression (1) below, and the order of the square matrix is four, which is the number of the sensor elements PD, for example. The certain code is a code based on a square matrix having "1" or "−1" or "1" or "0" as elements in which any two different rows form an orthogonal matrix, or an Hadamar matrix, for example. The diagonal element "−1" of the square matrix of Expression (1) below is different from the element "1", which is other than the diagonal element of the square matrix. The CDM access circuit 15c applies the gate drive signal VGCL to the gate line GCL corresponding to the element "1", which is other than the diagonal element of the square matrix based on the square matrix of Expression (1) below. The sensor element PD corresponding to the element "1" is selected as the sensor element PD of a first object to be selected. In a period during which the sensor element PD of the first object to be selected is selected, the gate drive signal VGCL is not applied to the gate line GCL corresponding to the element "−1", and the sensor element PD corresponding to the element "−1" is not selected.

$$\begin{pmatrix} -1 & 1 & 1 & 1 \\ 1 & -1 & 1 & 1 \\ 1 & 1 & -1 & 1 \\ 1 & 1 & 1 & -1 \end{pmatrix} \begin{pmatrix} 1.8 \\ 2.2 \\ 1.8 \\ 1.8 \end{pmatrix} = \begin{pmatrix} 4.0 \\ 3.2 \\ 4.0 \\ 4.0 \end{pmatrix} \qquad (1)$$

When a part Fg-a to be detected of the finger Fg or the like (recesses and protrusions and/or veins of the finger Fg, for example) is present in the sensor element PD-2 out of the sensor elements PD, the intensity of the light L2 applied to the sensor PD-2 is different from that of the other sensor elements PD. Thus, a differential voltage occurs in the detection signal Vdet output from the sensor elements PD (the differential voltage is 20%, for example).

In a first time slot, the sensor elements PD-2, PD-3, and PD-4, which correspond to the element "1" on the first row of the square matrix of Expression (1), are selected as the first object to be selected. A first detection signal Vdet1, which is detected by the detection circuit 40 in the first time slot, is (0)+(0.8)+(1)+(1)=2.8. Next, in a second time slot, the sensor element PD-1, which corresponds to the element "−1" on the first row of the square matrix of Expression (1), is selected as a second object to be selected. A second detection signal Vdet2, which is detected by the detection circuit 40 in the second time slot, is (1)+(0)+(0)+(0)=1. From the difference between the first detection signal Vdet1=2.8 detected in the first time slot and the second detection signal Vdet2=1.0 detected in the second time slot, the signal processor 44 computes a third detection signal Vdet3=1.8.

In a third time slot, the sensor elements PD-1, PD-3, and PD-4, which correspond to the element "1" on the second row of the square matrix of Expression (1), are selected as the first object to be selected. In a fourth time slot, the sensor element PD-2, which corresponds to the element "−1" on the second row of the square matrix of Expression (1), is selected as the second object to be selected. From the difference between the first detection signal Vdet1=3.0 detected in the third time slot and the second detection signal Vdet2=0.8 detected in the fourth time slot, the signal processor 44 computes the third detection signal Vdet3=2.2. The same is performed in a fifth time slot to an eighth time slot, and the signal processor 44 computes four third detection signals Vdet3=(1.8, 2.2, 1.8, 1.8) in the first time slot to the eighth time slot.

The signal processor 44 transmits the third detection signals Vdet3 as the acquired living body information BI-D to the authentication device 3 (refer to FIG. 1). The living body information processing circuit 33 multiplies the third detection signals Vdet3 by the square matrix of Expression (1) to perform decoding. Thus, the living body information processing circuit 33 computes vdet4=(4.0, 3.2, 4.0, 4.0) as decoded signals Vdet4. The living body information processing circuit 33 computes the living body information BI-DC after conversion based on the decoded signals Vdet4 and can thus recognize the presence or absence of the part Fg-a to be detected at the position of the sensor element PD-2. Thus, the sensor 6 can perform detection with detection sensitivity four times that of time division multiplexing (TDM) drive by the CDM drive.

Without being limited to causing the first to nth rows of a matrix to correspond to the first to nth gate lines GCL of the sensor 6, it can also be possible to cause the first row of the matrix to correspond to an Xth gate line GCL of the sensor 6 and to cause the second row of the matrix to correspond to a Yth one, which is not adjacent to the Xth one, in accordance with a table separately provided. Thus, the correspondence relation between the rows of the matrix and the gate lines GCL of the sensor 6 is caused to follow a rule separately set, whereby the security of the output of the sensor 6 can be increased. Similarly, it can also be possible to cause a relation between the columns of the matrix and the signal lines SGL of the sensor 6 to follow a rule separately set to perform drive such that even for columns adjacent to each other on the matrix, the signal lines SGL of the sensor 6 are not adjacent to each other. The rules separately set shown above may be held by the authentication device 3 to be included in the sensor control code SC and transferred to the detection device 2; alternatively, both the authentication device 3 and the detection device 2 may hold a table storing therein a plurality of the rules, and an instruction about which rule in the table is selected may be included in the sensor control code SC. Decoding may be divided into a plurality of procedures, in which part of the decoding may be performed by the signal processor 44 and then transmitted to the authentication device 3, and the living body information processing circuit 33 of the authentication device 3 may execute the rest of the decoding. In this case, an instruction about until what stage is performed by the signal processor 44 may be included in the sensor control code SC. The detection device 2 may perform the decoding until sorting data read by the sensor (RAW data) into a matrix by a certain method, whereas the authentication device 3 may perform matrix computation on the sorted data, for example. More specifically, as in FIG. 9, when the gate lines GCL corresponding to the first to Mth rows of the matrix are selected and driven in each of the period t(1) to a period t(M), and the signal line SGL1 to the signal line SGL6 are successively selected in each period t, the detection device 2 may sort data corresponding to the first to Mth rows of the matrix for each of the signal lines SGL, and the authentication device 3 may perform the matrix computation on the data sorted for each of the signal lines SGL for each of the signal lines SGL. The matrix may be decomposed, and the matrix computation may be performed by both the authentication device 3 and the detection device 2.

FIG. 12 is only by way of example and can be changed as appropriate. The certain code may be defined by a square matrix H shown by Expression (2) below, for example. The CDM drive and the CDM access circuit 15c are described in Japanese Patent Application No. 2018-005178, for example, and the description of Japanese Patent Application No. 2018-005178 is included in the present embodiment, and the description is omitted.

$$H = \begin{pmatrix} 1 & 1 & 1 & 1 \\ 1 & -1 & 1 & -1 \\ 1 & 1 & -1 & -1 \\ 1 & -1 & -1 & 1 \end{pmatrix} \quad (2)$$

Figure 13:
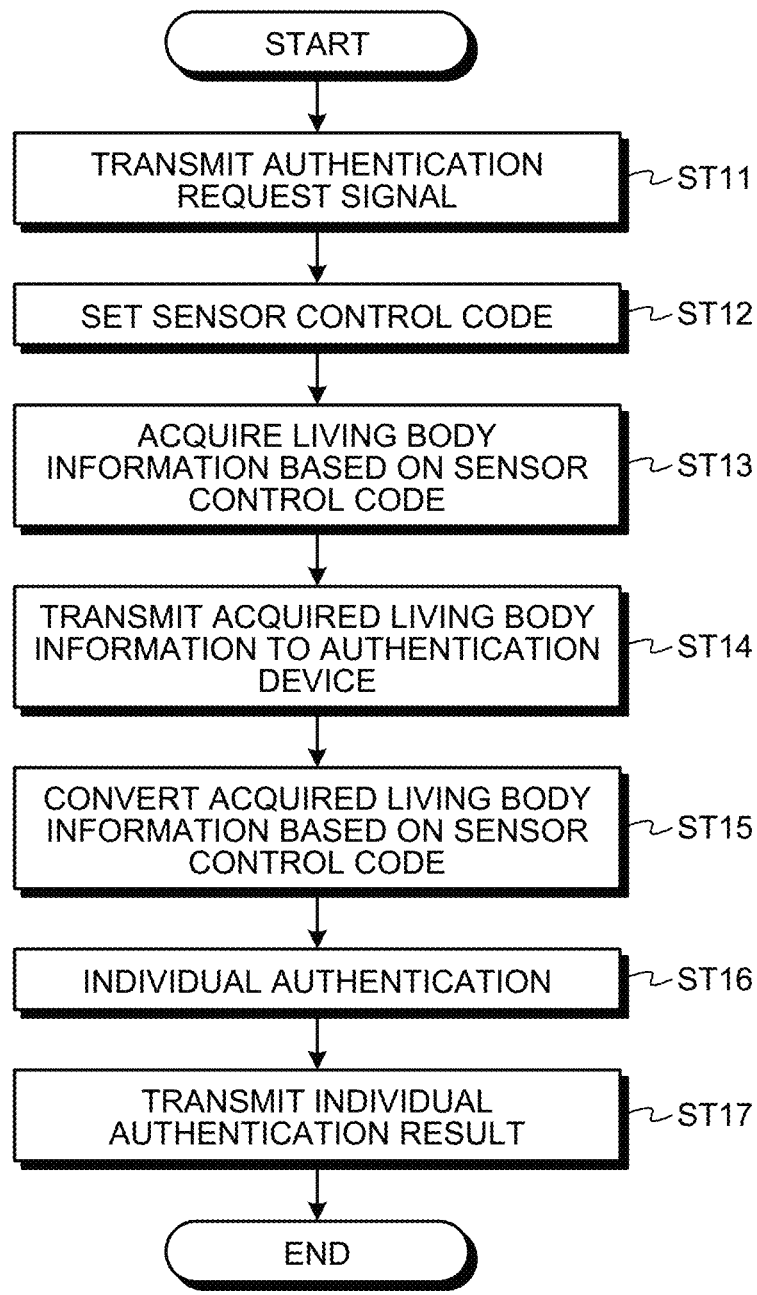
FIG. 13 is a flowchart of a method of personal authentication.
Figure 14:
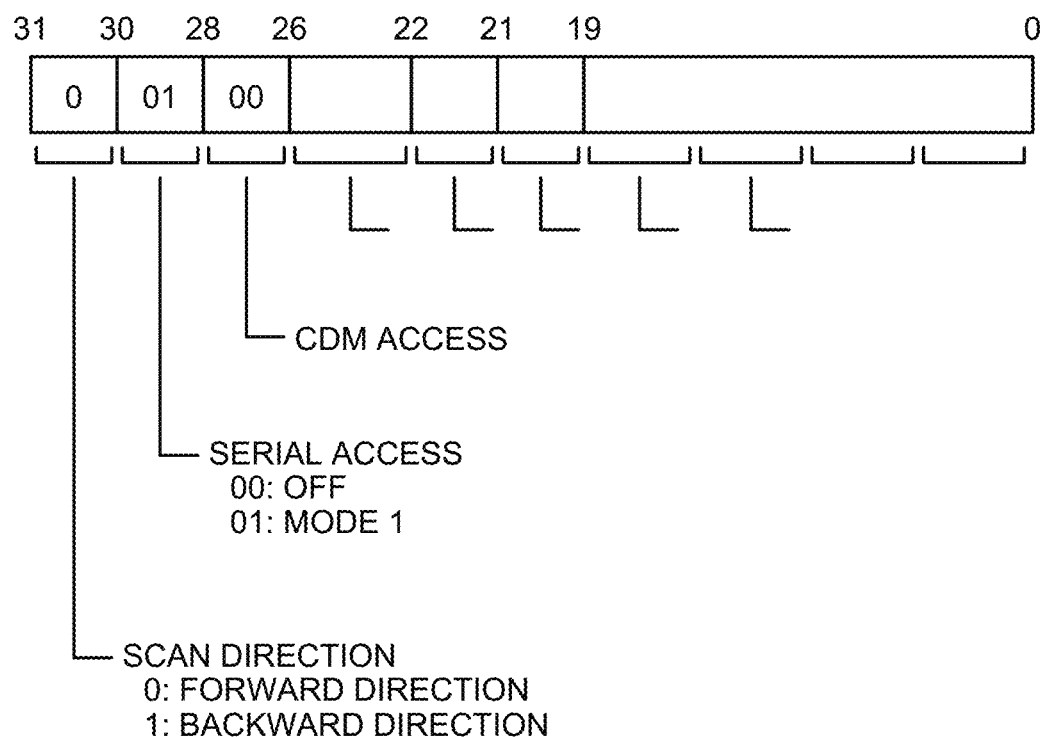
FIG. 14 is a table of an example of a sensor control code database.
Figure 15:
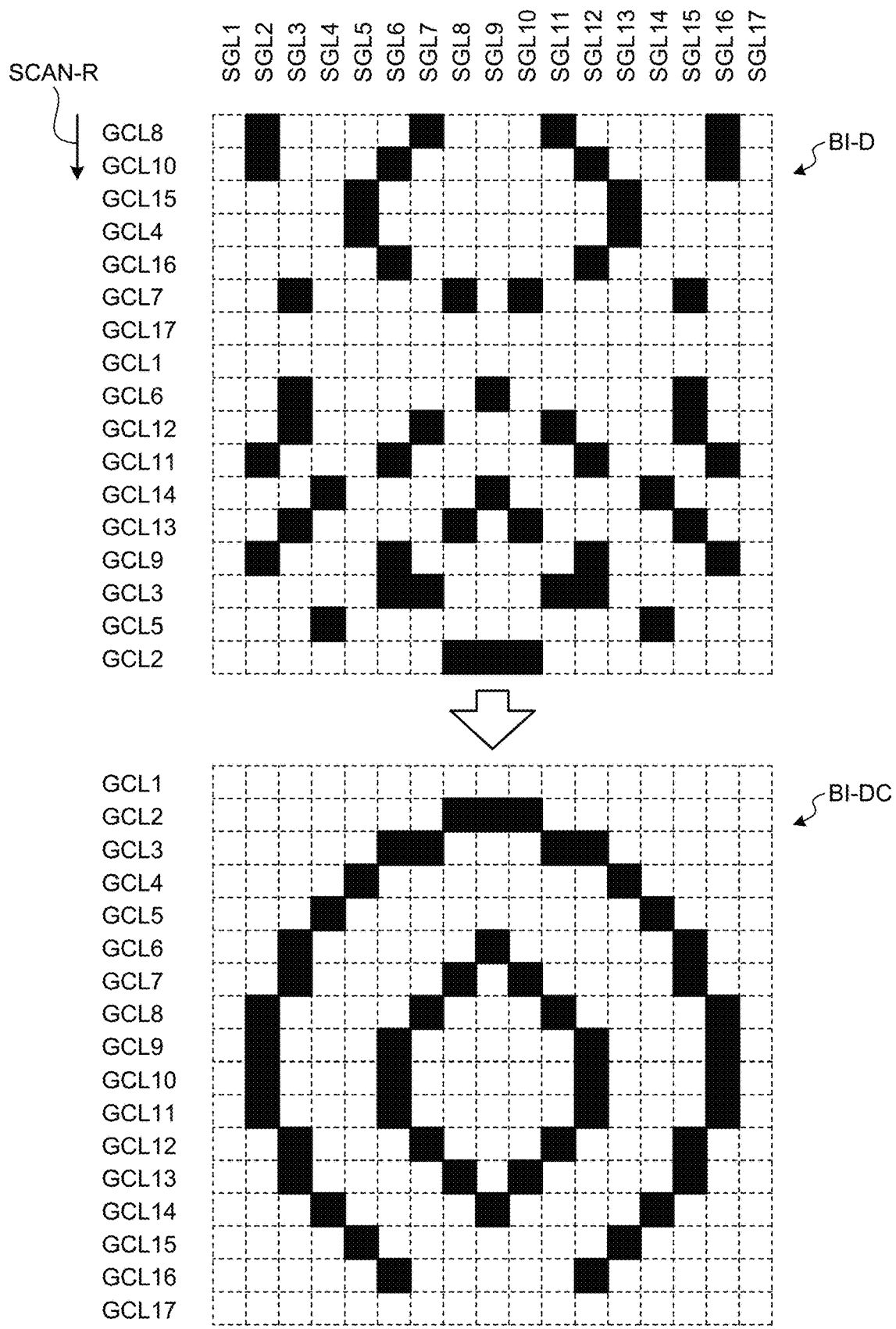
FIG. 15 is an illustrative diagram for illustrating an example of a method for converting acquired living body information by a living body information processing circuit.

The following describes a method of authentication by the biometric authentication system 1 with reference to FIG. 1, FIG. 6, FIG. 11, and FIG. 13 to FIG. 15. FIG. 13 is a flowchart of a method of personal authentication. FIG. 14 is a table of an example of a sensor control code database. FIG. 15 is an illustrative diagram for illustrating an example of a method for converting the acquired living body information by the living body information processing circuit.

As illustrated in FIG. 13, the detection control circuit 102 transmits an authentication request signal to the authentication device 3 (Step ST11). The detection control circuit 102 transmits the authentication request signal when the sensor 6 detects contact or proximity of the finger Fg or the like. Without being limited to this example, the detection control circuit 102 may transmit the authentication request signal based on a detection signal from the touch sensor of the display panel 5. The detection control circuit 102 transmits various kinds of information such as information (ID) of a user and the type of the living body information to be detected together with the authentication request signal. The authentication request may be transmitted from the authentication device 3 to the detection device 2 by a trigger such as proximity of the detection device 2 to the authentication device 3.

When receiving the authentication request signal, the authentication control circuit 31 transmits the authentication request signal and the various kinds of information to the sensor control code setter 32. The sensor control code setter 32 sets the sensor control code SC based on the various kinds of information (Step ST12). The sensor control code setter 32 determines a certain selection mode out of the selection modes of the sensor control code database 36a to set the sensor control code SC for driving the sensor 6 and the illumination device 7. The authentication control circuit 31 transmits the sensor control code SC received from the sensor control code setter 32 to the detection device 2 via the communicator 37.

As illustrated in FIG. 14, the sensor control code database 36a includes the sensor control code SC for controlling the sensor elements PD and the illumination device 7. The sensor control code SC includes the selection modes for controlling driving of the gate lines GCL by the gate line drive circuit 15. The sensor control code database 36a stores therein a scan direction code, a serial access code, a CDM access code, a random access code, and the like as the selection modes, for example.

Out of the selection modes, the scan direction code, for example, is a signal for controlling a scan direction of the gate lines GCL. The gate line drive circuit 15 scans the gate lines GCL from the gate line GCL1 to the gate line GCL(M) along a forward direction SCAN1 (refer to FIG. 11) based on a scan direction code of "0". The gate line drive circuit 15 scans the gate lines GCL from the gate line GCL(M) to the gate line GCL1 along a backward direction SCAN2 (refer to FIG. 11) based on a scan direction code of "1".

Out of the selection modes, the serial access code is a signal for controlling the number of the gate lines GCL simultaneously selected. The gate line drive circuit 15 operates the serial access circuit 15a based on a serial access code of "01" or "10". The serial access circuit 15a scans the gate lines GCL successively one by one based on a serial access code of "01" (Mode 1). The serial access circuit 15a successively scans the gate lines GCL in a bundle based on a serial access code of "10" (Mode 2).

The CDM access code is a signal for controlling the CDM drive by the gate line drive circuit 15. The CDM access code includes information on a code selecting a certain gate line GCL out of the gate lines GCL. The gate line drive circuit 15 operates the CDM access circuit 15c based on a CDM access code of "01" or "10". The CDM access circuit 15c selects the gate lines GCL based on the certain code (the code shown in Expression (1), for example) to perform the CDM drive based on a CDM access code of "01" (Mode 1). The CDM access circuit 15c selects the gate lines GCL based on the certain code different from that of Mode 1 (the code shown in Expression (2), for example) to perform the CDM drive based on a CDM access code of "10" (Mode 2).

The random access code is a signal for randomly driving the gate lines GCL by the gate line drive circuit 15. The gate line drive circuit 15 operates the random access circuit 15b based on a random access code of "01" or "10". The random access circuit 15b randomly scans the gate lines GCL based on a random access code of "01" (Mode 1). The random access circuit 15b randomly scans the gate lines GCL for each of a certain number of gate lines GCL based on a random access code of "10" (Mode 2).

The sensor control code SC includes information on the wavelength of the light L1 applied from the illumination device 7. The illumination device 7 switches light sources (LEDs, for example) to be turned on based on an illumination device code. The illumination device 7 applies the light L1 of visible light based on an illumination device code of "0", for example. The illumination device 7 applies the light L1 of near-infrared light based on an illumination device code of "1".

The sensor control code SC includes a plurality of selection modes of the signal lines SGL. The signal line selection circuit 16 switches a method of connection between the signal lines SGL and the detection circuit 40 based on a signal line access code. The signal line selection circuit 16 couples the selected signal lines SGL to the detection circuit 40 in a time division manner as illustrated in FIG. 9 based on a signal line access code of "00" (Mode 1), for example. The signal line selection circuit 16 simultaneously couples the selected signal lines SGL to the detection circuit 40 as illustrated in FIG. 10 based on a signal line access code of "01" (Mode 2), for example. The signal line selection circuit 16 may CDM drive the signal lines SGL based on a signal line access code of "10" (Mode 3), for example.

The sensor control code setter 32 sets a CDM access code of "01" or "10" in the case of fingerprint detection, for example. Alternatively, the sensor control code setter 32 may set the serial access code, the CDM access code, or the random access code in any manner. The sensor control code setter 32 sets an illumination device code of "0" in the case of fingerprint detection, for example, and sets an illumination device code of "1" in the case of detection of the venous pattern or the like, for example. The sensor control code setter 32 may select the selection modes in accordance with time, weather, or the like. Selection can be made as appropriate; fingerprint authentication, which is less affected by infrared rays, is selected in a situation in which the detection device 2 is placed, or under direct sunlight, for example. When authentication once fails, and authentication is performed again, a mode that is considered not to cause a failure may be selected. When authentication fails on driving with a scan direction of a forward direction, for example, scanning can be performed in a backward direction next time.

Next, the detection control circuit 102 drives the sensor 6 and the illumination device 7 based on the sensor control code SC to acquire the living body information (Step ST13). The upper drawing in FIG. 15 illustrates the acquired living body information BI-D detected based on a random access code of "01". The random access circuit 15b randomly drives the gate lines GCL in order of gate lines GCL8, GCL10, GCL15, . . . as shown by the arrow SCAN-R in FIG. 15 based on the sensor control code SC.

The detection circuit 40 causes the memory 21 to successively store therein the signal based on the detection signal Vdet of the sensor elements PD in order of the gate lines GCL scanned. Thus, the detection device 2 can acquire the acquired living body information BI-D. That is to say, the acquired living body information BI-D is acquired with an arrangement corresponding to driving of the sensor elements PD, that is, the order of the gate lines GCL scanned based on the sensor control code SC without the signals of the sensor elements PD rearranged. The acquired living body information BI-D is information different from the living body information of an actual user, and the living body information of the actual user is not held by the detection device 2.

FIG. 15 illustrates the acquired living body information BI-D in the case of the random access; even when the same object to be detected is detected, the acquired living body information BI-D with different patterns is detected depending on a combination of the serial access code, the CDM access code, the random access code, and the scan direction code.

FIG. 15 illustrates a case in which the signal lines SGL are coupled to the detection circuit 40 successively one by one; this is not limiting, and the operation of the signal line selection circuit 16 (the order, the number, and the like of connection between the signal lines SGL and the detection circuit 40) may vary based on the signal line access code. The acquired living body information BI-D with different patterns is detected depending on a combination of the serial access code, the CDM access code, the random access code, the scan direction code, and the signal line access code.

Next, the detection control circuit 102 transmits the acquired living body information BI-D to the authentication device 3 via the communicator 22 (Step ST14). That is to say, in the biometric authentication system 1, the living body information of the actual user is not transmitted or received between the detection device 2 and the authentication device 3. That is to say, when the detection device 2 outputs the acquired living body information BI-D acquired in accordance with the selection modes to the outside, the acquired living body information BI-D is output in such a condition that is unable to be restored without the sensor control code SC.

The living body information processing circuit 33 receives the acquired living body information BI-D. The living body information processing circuit 33 receives the information on the sensor control code SC from the sensor control code setter 32. The living body information processing circuit 33 converts the acquired living body information BI-D acquired in accordance with the selection modes based on the sensor control code SC (Step ST15). Specifically, as illustrated in FIG. 15, the living body information processing circuit 33 arranges the acquired living body information BI-D arranged in order of the scanned gate lines GCL in order of the arrangement of the gate lines GCL like the gate lines GCL1, GCL2, . . . , GCL 17 based on the sensor control code SC. Thus, the living body information processing circuit 33 can acquire the converted living body information BI-DC.

The authentication circuit 35 compares the converted living body information BI-DC received from the living body information processing circuit 33 and the registered living body information BI-R received from the memory 36 with each other to perform individual authentication (Step ST16).

The authentication control circuit 31 transmits an individual authentication result received from the authentication circuit 35 to the detection device 2 (Step ST17). The detection device 2, when identifying the user based on the individual authentication result, executes certain processing (permission to access an apparatus in which the detection device 2 is installed, for example).

As described in the foregoing, the biometric authentication system 1 has the detection device 2 acquiring the living body information and the authentication device 3 coupled to the detection device 2 via the network NW and performing personal authentication. The detection device 2 has the sensor elements PD, the gate lines GCL and the signal lines SGL, and the gate line drive circuit 15. The gate lines GCL and the signal lines SGL are coupled to the sensor elements PD via the first switching elements Tr. The gate line drive circuit 15 scans the gate lines GCL. The authentication device 3 compares the acquired living body information BI-D acquired by the detection device 2 and the stored registered living body information BI-R with each other to perform personal authentication. The authentication device 3 has the memory 36, the sensor control code setter 32, and the communicator 37. The memory stores therein the sensor control code SC controlling the sensor elements PD of the detection device 2 and the registered living body information BI-R registered in advance. When receiving the authentication request signal to start authentication from the detection device 2, the sensor control code setter 32 sets the sensor control code SC. The communicator 37 transmits the sensor control code SC to the detection device 2. The sensor control codes SC include the selection modes of the gate lines GCL, and the gate line drive circuit 15 scans the gate lines GCL based on the sensor control code SC received from the authentication device 3.

The authentication device 3 further has the living body information processing circuit 33 and the authentication circuit 35. The living body information processing circuit 33 converts the acquired living body information BI-D acquired in accordance with the selection modes based on the sensor control code SC. The authentication circuit 35 compares the living body information BI-DC converted by the living body information processing circuit 33 and the registered living body information BI-R with each other.

Thus, the sensor elements PD operate based on the selection modes of the sensor control code SC received from the authentication device 3. The detection device 2 transmits the acquired living body information BI-D acquired by driving by the sensor control code SC to the authentication device 3. The registered living body information BI-R is stored in the authentication device 3. Thus, a terminal having the detection device 2 stores therein the acquired living body information BI-D different from the actual living body information, and the detection device 2 does not hold the actual living body information or the registered living body information BI-R. Transmission and reception of the actual living body information are not performed between the detection device 2 and the authentication device 3. Thus, the biometric authentication system 1 can increase the confidentiality of the living body information. That is to say, the detection device 2 transfers the living body information to the authentication device 3 in an encrypted (encoded) manner. The detection device 2 can also acquire information indicating that a user is currently conducting living body activities such as the blood flow information or the pulsation of the user. These pieces of information indicating living body activities can also be encrypted. The data on a fingerprint, veins, or the like for biometric authentication can be transmitted to the authentication device 3 in an encrypted manner, whereas the information indicating living body activities can be transferred thereto without being encrypted.

The acquired living body information BI-D is acquired by driving of the sensor 6 based on the sensor control code SC, and thus even when the sensor control code SC leaks, conversion of the acquired living body information BI-D is difficult without the information on the sensor 6. Consequently, the biometric authentication system 1 can increase the confidentiality of the living body information compared with a method performing encryption by what is called a cryptographic key or the like.

(First Modification)

Figure 16:
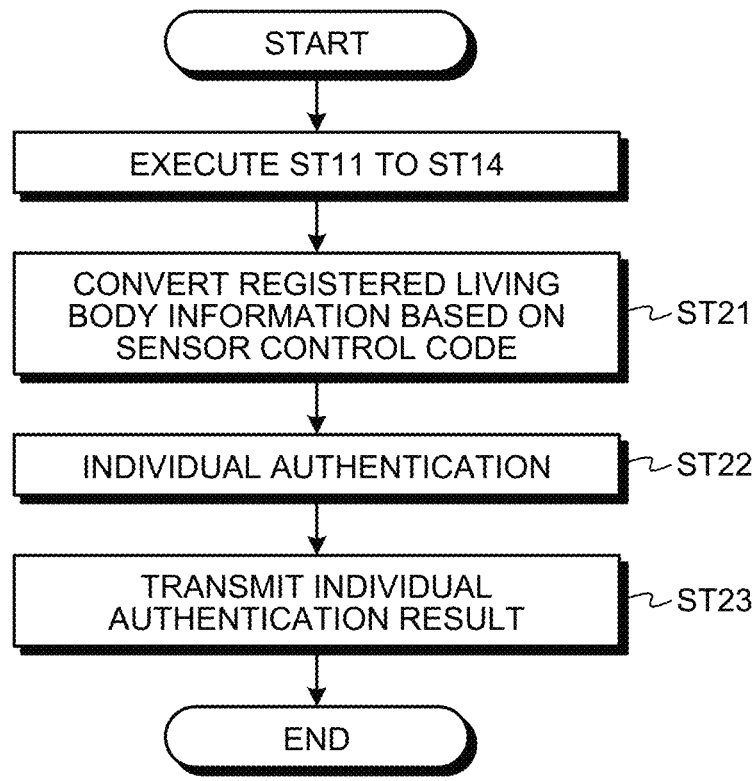
FIG. 16 is a flowchart of a method of personal authentication according to a first modification.

FIG. 16 is a flowchart of a method of personal authentication according to a first modification. Although FIG. 13 illustrates a case in which the living body information processing circuit 33 converts the acquired living body information BI-D based on the sensor control code SC, this is not limiting.

As illustrated in FIG. 16, the biometric authentication system 1 executes Step ST11 to Step ST14 like FIG. 13. The living body information processing circuit 33 receives the registered living body information BI-R stored in the memory 36 and converts the registered living body information BI-R based on the sensor control code SC (Step ST21). When the sensor control code SC is the random access code, for example, the living body information processing circuit 33 converts the registered living body information BI-R in the same order as the order of random driving of the gate lines GCL by the random access circuit 15*b*.

The authentication circuit 35 compares the acquired living body information BI-D received from the detection device 2 and the converted registered living body information BI-R received from the living body information processing circuit 33 with each other to perform individual authentication (Step ST22). The authentication control circuit 31 transmits an authentication result received from the authentication circuit 35 to the detection device 2 (Step ST23).

In the first modification, conversion of the acquired living body information BI-D is not performed in the authentication device 3. Thus, the living body information processing circuit 33 can execute conversion of the registered living body information BI-R shown at Step ST21 concurrently with Step ST13 (refer to FIG. 13), in which the detection device 2 acquires the acquired living body information BI-D.

(Second Modification)

Figure 17:
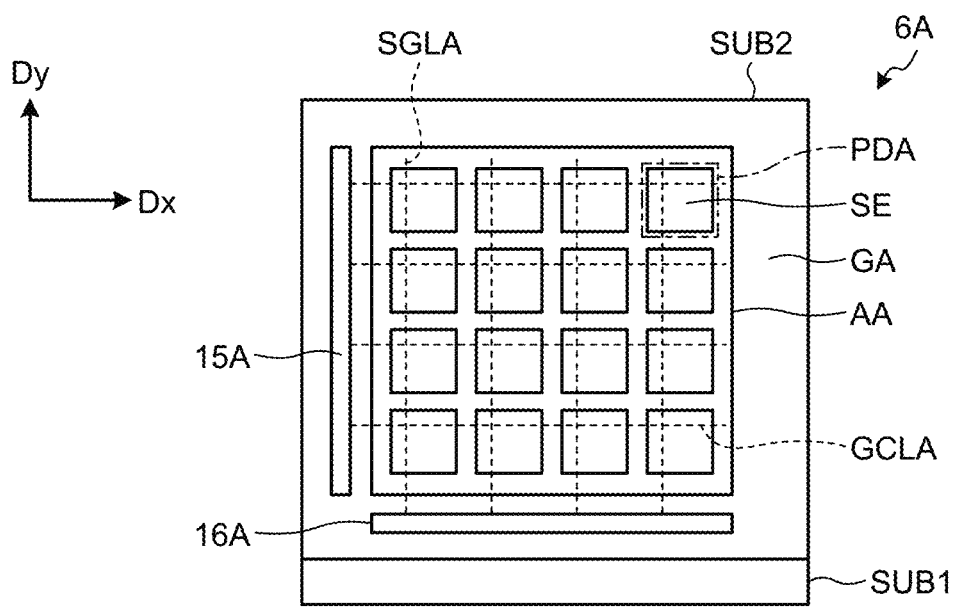
FIG. 17 is a plan view of a sensor according to a second modification.

FIG. 17 is a plan view of a sensor according to a second modification. This sensor 6A of the second modification is a capacitance type sensor. As illustrated in FIG. 17, the sensor 6A of the second modification has a first substrate SUB1, a second substrate SUB2, a plurality of sensor elements PDA, a plurality of gate lines GCLA, a plurality of signal lines SGLA, a gate line drive circuit 15A, and a signal line selection circuit 16A.

The sensor elements PDA have respective sensor electrodes SE, which each output the detection signal Vdet corresponding to a capacitance change with the finger Fg. The sensor electrodes SE are provided in a matrix (row-column configuration) in the display area AA of the first substrate SUB1. Although in FIG. 17 the sensor electrodes SE are arranged in four rows and four columns, it is illustrated only by way of example, and this is not limiting. The area, the placement pitch, and the number of the sensor electrodes SE can be changed in accordance with the resolution of detection or the like.

The gate lines GCLA extend in the first direction Dx and couple the sensor electrodes SE arranged in the first direction Dx and the gate line drive circuit 15A to each other. The signal lines SGLA extend in the second direction Dy and couple the sensor electrodes SE arranged in the second direction Dy and the signal line selection circuit 16A to each other. The sensor elements PDA have a detection switch DS1 coupled to the sensor electrodes SE, for example, and the gate lines GCLA and the signal lines SGLA are coupled to the sensor electrodes SE via switch elements. The gate line drive circuit 15A supplies a selection signal via the gate lines GCLA based on the sensor control code SC received from the authentication device 3 to select the sensor electrodes SE to be driven. In other words, the gate line drive circuit 15A selects sensor electrode SE rows arranged in the second direction Dy. The signal line selection circuit 16A supplies a drive signal for fingerprint detection to the sensor electrodes SE via the signal lines SGLA or receives the detection signal Vdet detected by the sensor electrodes SE to output the detection signal Vdet to the detection circuit 40 (refer to FIG. 4). In other words, the signal line selection circuit 16A selects sensor electrode SE columns arranged in the first direction Dx.

Figure 18:
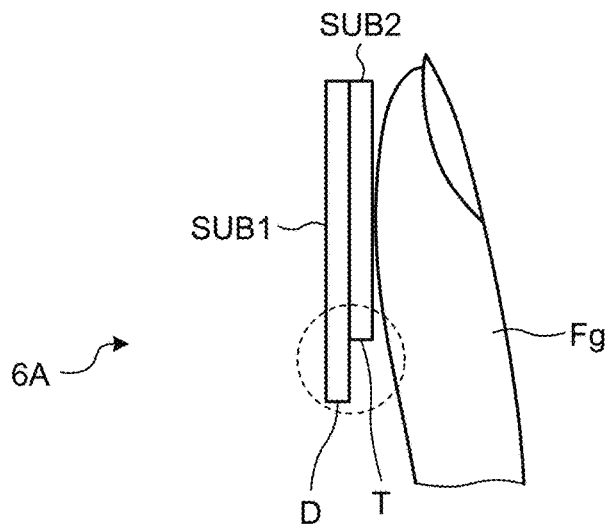
FIG. 18 is a side view of the sensor according to the second modification.

FIG. 18 is a side view of the sensor according to the second modification. As illustrated in FIG. 18, the second substrate SUB2 is overlaid on the first substrate SUB1. That is to say, the sensor electrodes SE are held between the two substrates. The first substrate SUB1 and the second substrate SUB2 are each a glass substrate or a resin substrate, for example. The second substrate SUB2 may be a coating layer formed of an inorganic insulating film or an organic insulating film.

The second substrate SUB2 has a smaller area of a principal face of the substrate than that of the first substrate SUB1. A step D is formed near an end T of the second substrate SUB2. Signal wires, a flexible board, terminals (connectors), and the like can be placed at an area of the first substrate SUB1 on which the second substrate SUB2 is not superimposed.

In the sensor 6A, when the finger Fg is in proximity to or in contact with the second substrate SUB2, the detection signal Vdet corresponding to the capacitance change between the sensor electrodes SE and the finger Fg by recesses and protrusions on the surface of the finger Fg is output from the sensor electrodes SE.

Figure 19:
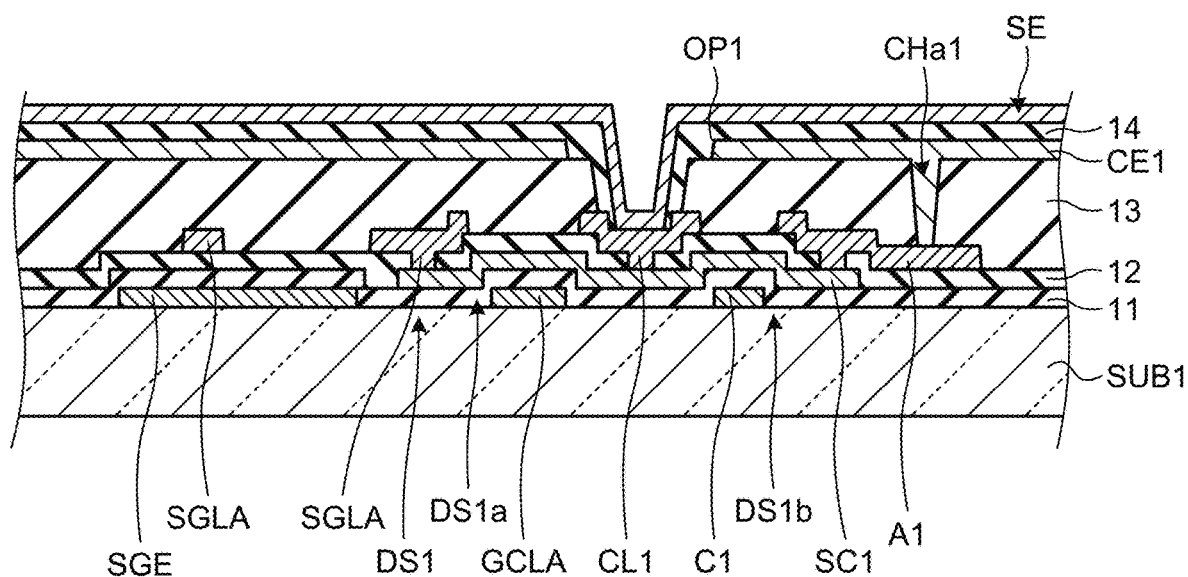
FIG. 19 is a partially enlarged view of a sectional view of the sensor according to the second modification.

FIG. 19 is a partially enlarged view of a sectional view of the sensor according to the second modification. FIG. 19 is a schematic enlarged view of a sectional view of the sensor 6A in FIG. 17 along the first direction Dx. As illustrated in FIG. 19, further provided on the first substrate SUB1 are the detection switch DS1, an auxiliary guard electrode SGE, a control line C1, an auxiliary wire A1, a conductive layer CL1, and a counter electrode CE1. The counter electrode CE1 faces a sensor electrode SE via an insulating film 14. The counter electrode CE1 is provided above the detection switch DS1 via an insulating film 13.

The detection switch DS1 includes a first switching element DS1*a* and a second switching element DS1*b*. Stacked on each other on the first substrate SUB1 are the gate lines GCLA and the control line C1, an insulating film 11, a semiconductor layer SC1, an insulating film 12, and the signal lines SGLA and the auxiliary wire A1 in this order. The first switching element DS1*a* and the second switching element DS1*b* have the semiconductor layer SC1 continuously formed. The sensor electrode SE is coupled to the semiconductor layer SC1 via the conductive layer CL1.

The first switching element DS1*a* is a switching element switching a connection state between the sensor electrodes SE and the signal lines SGLA based on the selection signal supplied to the gate lines GCLA. The second switching element DS1*b* is a switching element switching a connection state between the sensor electrodes SE and the counter electrode CE1 based on a control signal supplied to the control line C1. The counter electrode CE1 is coupled to the auxiliary wire A1 via a contact hole CHa1 provided in the insulating film 13. The auxiliary wire A1 is coupled to the semiconductor layer SC1.

The first switching element DS1*a* and the second switching element DS1*b* operate such that when either one of them turns on (a conduction state), the other of them turns off (a non-conduction state). That is to say, the sensor electrodes SE selected by the gate line drive circuit 15A based on the sensor control code SC turn on the first switching element DS1a and turn off the second switching element DS1b and are electrically coupled to the signal lines SGLA. Thus, the drive signal is supplied to the sensor electrodes SE from the signal lines SGLA, and the detection signal Vdet is output to the signal lines SGLA.

On the other hand, the sensor electrodes SE not selected turn off the first switching element DS1a and turn on the second switching element DS1b, and an active guard potential is supplied to the sensor electrodes SE from the auxiliary wire A1. The active guard potential is a potential synchronized with the drive signal of the sensor electrodes SE, for example. Thus, parasitic capacitance between the sensor electrodes SE not selected and the signal lines SGLA or the control line C1 can be reduced. The sensor electrodes SE not selected may be supplied with a fixed potential or may be a floating potential.

The auxiliary guard electrode SGE is provided between the signal lines SGLA and the first substrate SUB1. Thus, noise from a lower side of the first substrate SUB1 (an opposite face thereof from the face on which the sensor electrodes SE are formed) toward the signal lines SGLA can be shielded.

In the second modification as well, the sensor electrodes SE are driven based on the selection modes of the sensor control code SC received from the authentication device 3. The detection device 2 transmits the acquired living body information BI-D from the sensor 6A acquired by driving by the sensor control code SC to the authentication device 3. That is to say, the detection device 2 transfers the living body information detected by the sensor 6A to the authentication device 3 in an encrypted (encoded) manner. Thus, the biometric authentication system 1 can increase the confidentiality of the living body information. The sensor 6A is not limited to self-capacitance type touch detection. The sensor 6A may execute mutual capacitance type touch detection. In this case, in the sensor 6A, drive electrodes and detection electrodes are provided in place of the sensor electrodes SE, a drive signal is supplied to the drive electrodes selected by a drive electrode selection circuit in place of the gate line drive circuit 15A, and the detection electrodes selected by a detection electrode selection circuit in place of the signal line selection circuit 16A output a detection signal changing along with the state of recesses and protrusions on the surface of the finger Fg or the like. At least one of the drive electrode selection circuit and the detection electrode selection circuit selects the drive electrodes or the detection electrodes based on the selection modes of the sensor control code SC received from the authentication device 3.

The preferred embodiments of the present disclosure have been described; the present disclosure is not limited to such embodiments. The details disclosed in the embodiments are only by way of example, and various modifications can be made in a range not departing from the gist of the present disclosure. Appropriate modifications made in the range not departing from the gist of the present disclosure naturally belong to the technical scope of the present disclosure.

What is claimed is:

1. A biometric authentication system comprising:
    a detection device configured to acquire living body information; and
    an authentication device coupled to the detection device via a network and configured to perform personal authentication, wherein
    the detection device has
    a plurality of sensor elements,
    a plurality of gate lines and a plurality of signal lines provided in correspondence with the sensor elements, and
    a gate line drive circuit scanning the gate lines,
    the authentication device has
    a memory storing therein a sensor control code controlling the sensor elements and registered living body information as living body information registered in advance,
    a sensor control code setter configured to set the sensor control code when receiving, from the detection device, an authentication request signal to start authentication, and
    a communicator configured to transmit the sensor control code to the detection device,
    the sensor control code includes a plurality of selection modes of the gate lines, and
    the gate line drive circuit scans the gate lines based on the selection modes of the gate lines included in the sensor control code received from the authentication device,
    the selection modes of the gate lines having at least two or more of information out of:
    information on a scan direction of the gate lines,
    information on a number of the gate lines that are simultaneously selected,
    information on a code selecting certain one or more gate lines out of the gate lines, and
    information randomly driving the gate lines.

2. The biometric authentication system according to claim 1, wherein the authentication device further has:
    a living body information processing circuit configured to convert acquired living body information acquired in accordance with the selection modes based on the sensor control code, and
    an authentication circuit configured to compare the living body information converted by the living body information processing circuit and the registered living body information with each other.

3. The biometric authentication system according to claim 1, wherein the authentication device further has:
    a living body information processing circuit configured to convert the registered living body information stored in the memory based on the sensor control code, and
    an authentication circuit configured to compare the registered living body information converted by the living body information processing circuit and acquired living body information acquired in accordance with the selection modes with each other.

4. The biometric authentication system according to claim 1, wherein the sensor elements are photoelectric conversion elements outputting a signal corresponding to applied light.

5. The biometric authentication system according to claim 4, wherein
    the detection device has an illumination device applying the light, and
    the sensor control code includes information on a wavelength of the light applied from the illumination device.

6. The biometric authentication system according to claim 1, wherein
    the sensor control code includes a plurality of selection modes of the signal lines, and
    the detection device has a signal line selection circuit coupling a selected signal lines out of the signal lines and a detection circuit to each other based on the sensor control code.

7. A living body information detection device comprising:
a plurality of sensor elements;
a plurality of gate lines and a plurality of signal lines provided in correspondence with the sensor elements; and
a gate line drive circuit scanning the gate lines, wherein the gate line drive circuit scans the gate lines based on a plurality of selection modes of the gate lines included in a sensor control code that is supplied from outside, the selection modes of the gate lines having at least two or more of information out of:
information on a scan direction of the gate lines;
information on a number of the gate lines that are simultaneously selected;
information on a code selecting certain one or more gate lines out of the gate lines; and
information randomly driving the gate lines.

8. The living body information detection device according to claim 7, wherein when acquired living body information acquired in accordance with the selection modes is output to the outside, the acquired living body information is output in such a condition that is unable to be restored without the sensor control code.

9. The living body information detection device according to claim 7, wherein the sensor elements are photoelectric conversion elements outputting a signal corresponding to applied light.

10. The living body information detection device according to claim 9, further comprising an illumination device applying the light, wherein the sensor control code includes information on a wavelength of the light applied from the illumination device.

11. The living body information detection device according to claim 7, further comprising a signal line selection circuit coupling the signal lines and a detection circuit to each other based on the sensor control code, wherein the sensor control code includes a plurality of selection modes of the signal lines.

* * * * *